US010191062B2

(12) United States Patent
Pearson et al.

(10) Patent No.: US 10,191,062 B2
(45) Date of Patent: Jan. 29, 2019

(54) MODEL GUT SYSTEM

(71) Applicant: University of Newcastle Upon Tyne, Newcastle Upon Tyne (GB)

(72) Inventors: Jeff Pearson, Newcastle Upon Tyne (GB); Iain Brownlee, Newcastle Upon Tyne (GB); Matt Wilcox, Newcastle Upon Tyne (GB); Peter Chater, Newcastle Upon Tyne (GB); David Houghton, Newcastle Upon Tyne (GB)

(73) Assignee: University of Newcastle Upon Tyne (GB)

( * ) Notice: Subject to any disclaimer, the term of this patent is extended or adjusted under 35 U.S.C. 154(b) by 0 days.

(21) Appl. No.: 15/039,172

(22) PCT Filed: Nov. 21, 2014

(86) PCT No.: PCT/GB2014/053449
§ 371 (c)(1),
(2) Date: May 25, 2016

(87) PCT Pub. No.: WO2015/075467
PCT Pub. Date: May 28, 2015

(65) Prior Publication Data
US 2017/0160283 A1 Jun. 8, 2017
US 2018/0067122 A9 Mar. 8, 2018

(30) Foreign Application Priority Data
Nov. 25, 2013 (GB) .................................. 1320781.6

(51) Int. Cl.
G09B 23/30 (2006.01)
G01N 33/66 (2006.01)
C12N 9/94 (2006.01)
C12Q 1/37 (2006.01)
G01N 33/68 (2006.01)
G01N 33/92 (2006.01)
C12Q 1/40 (2006.01)
C12Q 1/44 (2006.01)
G09B 9/00 (2006.01)

(52) U.S. Cl.
CPC ............... *G01N 33/66* (2013.01); *C12N 9/94* (2013.01); *C12Q 1/37* (2013.01); *C12Q 1/40* (2013.01); *C12Q 1/44* (2013.01); *G01N 33/68* (2013.01); *G01N 33/92* (2013.01); *G09B 9/00* (2013.01); *G09B 23/30* (2013.01); *G09B 23/303* (2013.01); *G09B 23/306* (2013.01)

(58) Field of Classification Search
None
See application file for complete search history.

(56) References Cited

U.S. PATENT DOCUMENTS

2007/0269795 A1 11/2007 Abromeit
2010/0105023 A1 4/2010 Aymard et al.
2012/0070813 A1* 3/2012 Wickham .............. B01F 5/0685
434/268
2017/0281091 A1* 10/2017 Shuck .................. A61B 5/6861

FOREIGN PATENT DOCUMENTS

| CN | 102329853 A | 1/2012 |
| EP | 2 178 066 A1 | 4/2010 |
| WO | WO 2007/010238 A1 | 1/2007 |
| WO | WO 2007/088062 A2 | 8/2007 |
| WO | WO 2011/012932 A1 | 2/2011 |
| WO | WO 2011/097266 A1 | 8/2011 |
| WO | WO 2012/101167 A1 | 8/2012 |

OTHER PUBLICATIONS

Peixoto F. et al. In vitro Bioaccessibility as a Tool to Test Improved Cultivars Performance with Higher Levels of Beta Carotene From Foods. BioChemistry 6(6)184-192, 2012. (Year: 2012).*
Ulleberg E. et al. Human Gastrointestinal Juices Intended for Use in In vitro Digestion Models. Food Digestion 2(1-3)52-61, Dec. 2011. (Year: 2011).*
Hur S. et al. In vitro Human Digestion Models for Food Applications. Food Chemistry 125(1)1-12, Mar. 1, 2011. (Year: 2011).*
Sarkar A. et al. Pancreatin Induced Coalescence of Oil in Water Emulsions in an In vitro Duodenal Model. International Dairy J 20:589-597, 2010. (Year: 2010).*
Hollebeeck et al., Development of a standardised human in vitro digestion protocol based on macronutrient digestion using response surface methodology. Food Chemistry. Jun. 1, 2013;138(2-3):1936-44.
Hur et al., Effects of various fiber additions on lipid digestion during in vitro digestion of beef patties. J Food Sci. Nov.-Dec. 2009;74(9):C653-7. doi: 10.1111/j.1750-3841.2009.01344.x.
Hur et al., In vitro human digestion models for food applications. Food Chemistry. 2011;125:1-12.
Kong et al., Disintegration of solid foods in human stomach. J Food Sci. Jun. 2008;73(5):R67-80. doi: 10.1111/j.1750-3841.2008.00766.x. Review.
Lebenthal et al., Enzyme therapy for pancreatic insufficiency: present status and future needs. Pancreas. Jan. 1994;9(1):1-12. Review.
Oomen et al., Development of an in vitro digestion model for estimating the bioaccessibility of soil contaminants. Arch Environ Contam Toxicol. Apr. 2003;44(3):281-7.

(Continued)

*Primary Examiner* — Ralph J Gitomer
(74) *Attorney, Agent, or Firm* — Wolf, Greenfield & Sacks, P.C.

(57) ABSTRACT

The invention relates to a Model Gut System (MGS) comprising a pancreatic phase consisting essentially of synthetic pancreatic juice comprising pancreatin and one or more suitable pancreatic diluent(s) at a pH from about 7 to about 9, preferably about 7.9 to about 8.2, and porcine bile.

18 Claims, 14 Drawing Sheets

(56) References Cited

OTHER PUBLICATIONS

Oomen et al., Effect of bile type on the bioaccessibility of soil contaminants in an in vitro digestion model. Arch Environ Contam Toxicol. Feb. 2004;46(2):183-8.

Reis et al., Influence of Surfactants on Lipase Fat Digestion in a Model Gastro-intestinal System. Food Biophys. Dec. 2008;3(4):370-81.

Sarkar et al., Pancreatin-induced coalescence of oil-in-water emulsions in an in vitro duodenal model. International Dairy Journal. Sep. 2010;20(9):589-97.

Vamanu et al., Viability of the Lactobacillus rhamnosus IL1 Strain in Simulated Gastrointestinal Conditions. International J of Pharmacology. 2010;6(5):732-7.

Adenugba et al., In vitro approaches to assess bioavailability and human gastrointestinal mobilization of food-borne polychlorinated biphenyls (PCBs). J Environ Sci Health B. Jun. 2008;43(5):410-21. doi: 10.1080/03601230802062257.

Guerra et al., Relevance and challenges in modeling human gastric and small intestinal digestion. Trends Biotechnol. Nov. 2012;30(11):591-600. doi: 10.1016/j.tibtech.2012.08.001. Epub Sep. 10, 2012. Review.

Werner et al., Bioaccessibility of carotenoids and vitamin e from pasta: evaluation of an in vitro digestion model. J Agric Food Chem. Feb. 23, 2011;59(4):1163-70. doi: 10.1021/jf103892y. Epub Jan. 25, 2011.

\* cited by examiner

MODEL GUT SYSTEM

RELATED APPLICATIONS

This application is a national stage filing under 35 U.S.C. § 371 of international application PCT/GB2014/053449, filed Nov. 21, 2014, which claims priority to UK Application No. 1320781.6, filed Nov. 25, 2013. Each of the prior applications is incorporated by reference in its entirety.

FIELD OF THE INVENTION

The present invention relates to a novel and inventive model gut system, which simulates the digestive tract from mouth to terminal small intestine. More particularly, the present invention relates to a novel and inventive model small intestine. Still more particularly, the present invention relates to a novel and inventive system for analysing carbohydrates, and/or triglycerides, and or proteins from a mixed physiological sample using the novel and inventive small intestine and/or model gut system.

BACKGROUND OF THE INVENTION

Despite current anti-obesity treatments the number of overweight and obese people is expected to rise to 2.3 billion and 700 million worldwide, respectively in the near future. Given the well understood risks of the development of further conditions associated with obesity, such as for example Type 2 diabetes, and heart disease, these figures effectively represent an economic healthcare time-bomb.

Currently there are many active development programmes looking both for potential treatments for obesity/weight maintenance, including both the search for new pharmaceutical or biopharmaceutical compounds having an impact upon the way in which food is internally processed by an obese subject, as well as the search for greater understanding of the nutritional value of foodstuffs, and particularly how they are digested.

A key part of the early development stages in the development of any new pharmaceutical or biopharmaceutical treatment for obesity it is necessary to assess the potential impact of test compounds on digestion. Whilst it is generally accepted that use of validated ex vivo model systems are of significant value within the development process as a replacement for animal models, both from an ethical and commercial perspective, to date it has not been possible to fully assess the potential impact of test compounds on the digestive system because there is presently no physiologically relevant in vitro model gut system (MGS) capable of simulating the digestive process of the gastrointestinal (GI) tract from the mouth to terminal small intestine. Thus there is a need for reliable, physiologically relevant in vitro model gut system (MGS) capable of simulating the digestive process of the gastrointestinal (GI) tract from the mouth to terminal small intestine. In addition there is a need for a model that can simulate carbohydrate, lipid and protein digestion simultaneously and which thus facilitates the study of whole food digestion, rather individual components.

The Applicant has recognised that in tandem with the need for new effective treatments for obesity, a parallel need exists to identify actives/compounds that positively or negatively influence the digestion of macromolecules, for example to provide improved understanding of the chemical and enzymatic digestion of the macronutrients in foodstuffs, and in particular the digestion of mixed macronutrient systems.

Prior to the present invention it has not been possible to analyse the chemical and enzymatic digestion of a mixed system of the macronutrients, triglycerides, protein and/or carbohydrate in an in vitro MGS cumulative of the mouth, stomach and small intestine.

SUMMARY OF THE INVENTION

A physiologically relevant in vitro Model Gut System (MGS) has been developed by the Applicant that simulates the digestive processes of the gastrointestinal (GI) tract from mouth to terminal small intestine. In this regard, the invention provides a novel and inventive assay system for analysing the digestion of carbohydrates, and/or triglycerides, and or proteins from a mixed physiological sample. In addition, the invention provides a novel and inventive model small intestine which simulates the digestive tract from mouth to terminal small intestine. Furthermore, the invention provides a novel and inventive system for analysing carbohydrates, and/or triglycerides, and/or proteins from a mixed physiological sample using the novel and inventive model small intestine. In addition, the invention provides a novel and inventive model gut system for analysing carbohydrates, and/or triglycerides, and or proteins from a mixed physiological sample using the novel and inventive model small intestine; a model stomach and a mouth model.

Methods for analysis of digestion products in samples from a simulated digestive environment is confounded by background interference in a mixed physiological sample. The presence of various chemicals, compounds and substrates results in cross reactivity with the assay reagents and can result in false positives or negatives and misreporting of data.

The aforementioned models and assay systems can, advantageously, be used to study the simultaneous chemical and enzymatic digestion of the macronutrients fat, protein and/or carbohydrate, and to analyse the effects of exogenous compounds on digestion of these macronutrients, with a view to developing novel therapeutics, bioactive foods or medical devices and/or understanding the mechanisms of digestion. The model systems of the invention have been validated using known inhibitors of macronutrient digestion, including orlistat, acarbose, pentosan polysulfate and soybean trypsin inhibitor. In addition, the model systems of the invention have been used successfully in the identification and characterisation of novel lipase inhibitors/activators of lipid, protein and carbohydrate digestions, including alginate, fucoidan and seaweed extracts.

The model systems of the invention were instrumental in the characterisation of specific alginates as inhibitors of lipid digestion, and these alginates have since shown clinical efficacy in human trials.

As with pharmacological studies, randomised, double blinded control trials in human populations are the gold standard of nutrition studies, however cost and complexity are often prohibitive. Smaller scale human studies can also be costly and difficult. The models and assay systems of the present invention provide a higher-throughput primary screening method by which compounds can be ruled in or out as effective therapeutic agents, and a system of analysis for looking at bioactive effects. The availability of a robust and low cost in vitro system, allowing prediction of the human in vivo effects of a compound (or a range of compounds) on digestion can be used to inform the dosage, and context (e.g. presence, absence or concentration of specific dietary components) in which a compound will have the desired effect, and the magnitude of this effect. This information is in turn useful in designing human trials.

The model systems and assays of the invention also provides an alternative to expensive and controversial animal testing. The model systems of the invention provide a physiological simulation of normal human digestion, which can be used to examine how novel pharmaceuticals and food additives affect digestion with a view to creating novel dietary intervention products. Model gut and/or model small intestine analysis provides a controlled, reproducible and cost-effective alternative to animal studies and a physiologically relevant model to inform and improve human studies.

The model gut system is a robust physiological simulation of the chemical and enzymatic aspects of digestion which can be used to model the effects of exogenous compounds on macronutrient digestion. Synthetic salivary and gastric juices are made up from purchased chemicals and enzymes according to physiological values from the literature. To model the more complex environment of the small intestine, fresh porcine bile is collected and pooled from abattoirs, and powdered porcine pancreatin is used for the complex mix of small intestinal enzymes. This means that a robust simulation of the chemical and enzymatic processes of digestion can be achieved.

According to one aspect the present invention provides a model gut system (MGS) comprising a pancreatic phase (model small intestine model) consisting essentially of synthetic pancreatic juice comprising pancreatin and one or more suitable pancreatic diluent(s) at a pH from about 7 to about 9, preferably about 7.9 to about 8.2, and porcine bile.

According to another aspect the present invention provides a model gut system (MGS) in accordance with the previous aspect which additionally comprises a gastric phase (stomach model).

According to a further aspect the present invention provides a model gut system (MGS) in accordance with the previous aspect which additionally comprises a gastric phase (stomach model) and a salivary phase (mouth model).

According to a particular aspect the present invention provides a screening method utilising the model gut system of the invention.

According to a further aspect there is provided a method of analysing triglycerides, and/or proteins from a mixed physiological sample comprising the steps of: i) treatment of a mixed physiological sample with trichloroacetic acid (TCA); ii) centrifugation of the resultant sample; and iii) analysis of the breakdown products of lipids, and/or proteins present in the supernatant of the resultant sample.

According to a further aspect there is provided a method of analysing carbohydrates, and/or triglycerides, and/or proteins from a mixed physiological sample comprising the steps of: i) treatment of a mixed physiological sample with trichloroacetic acid (TCA), optionally followed by centrifugation; treatment of the TCA-treated sample with potassium chloride (KCl), wherein the KCl treatment is present as an aqueous solvent solution; centrifugation of the resultant sample; and analysis of the breakdown products of carbohydrates, and/or lipids, and/or proteins present in the supernatant of the resultant sample.

According to a further aspect, the invention provides a model gut comprising: a salivary phase consisting essentially of synthetic saliva comprising an aqueous mixture of one or more suitable enzymes, and one or more suitable salivary diluent components at a pH in the range of from about 5 to 9; a gastric phase wherein the gastric phase comprises: consisting essentially of synthetic gastric juice comprising an aqueous mixture of gastric lipase, pepsin and one or more suitable gastric diluent components, at a pH from about 1.5 to about 3.5 and a pancreatic phase, a pancreatic phase consisting essentially of synthetic pancreatic juice comprising pancreatin and one or more suitable pancreatic diluent(s) at a pH from about 7 to about 9, preferably about 7.9 to about 8.2, and porcine bile.

According to a yet further aspect the present invention provides kits for the analysis of the carbohydrate, and/or triglyceride, and/or protein in a mixed physiological sample comprising the Models of the invention.

According to yet a further aspect there is provided use of a model of the invention for analysing carbohydrates, and/or triglycerides, and/or proteins or breakdown products thereof.

According to yet a further aspect there is provided use of a model of the invention for simulating the digestion of an edible/potable substance.

BRIEF DESCRIPTION OF THE DRAWINGS

Embodiments of the invention are further described hereinafter with reference to the accompanying drawings, in which.

DETAILED DESCRIPTION

Figure 1:
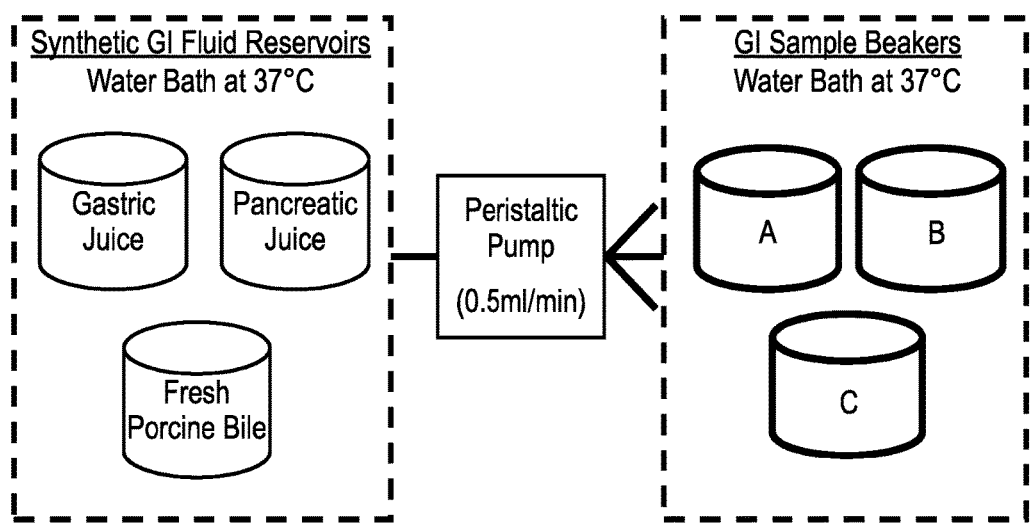
FIG. 1: Is a schematic of the equipment set-up of the model gut system of the invention.

As discussed hereinbefore, there is a need for reliable, physiologically relevant in vitro model gut system (MGS) capable of simulating the digestive process of the gastrointestinal (GI) tract from the mouth to terminal small intestine.

The Applicants have now developed a physiologically relevant in vitro Model Gut System (MGS) which simulates the digestive tract from mouth to terminal small intestine. As demonstrated by the results hereinafter, this model can be used to study the chemical and enzymatic digestion of the macronutrients, triglycerides, protein and carbohydrate and also to analyse the effects of exogenous compounds thereon.

The efficacy of the MGS has been demonstrated by the role it has played in building a case for the novel lipase inhibitor alginate as a weight loss treatment, which is now in human trials.

The novel and inventive MGS is a robust physiological simulation of the chemical and enzymatic aspects of digestion which can be used to model the effects of exogenous compounds on macronutrient digestion. To ensure that a robust simulation of the chemical and enzymatic processes of digestion can be achieved the MGS utilises synthetic salivary, gastric juice and pancreatic juice.

In a first aspect the invention provides a model gut system (MGS) comprising a pancreatic phase consisting essentially of synthetic pancreatic juice comprising pancreatin and one or more suitable pancreatic diluent(s) at a pH from about 7 to about 9, preferably about 7.9 to about 8.2, and bile, preferably porcine bile.

In one embodiment the MGS further comprises a gastric phase consisting essentially of synthetic gastric juice comprising an aqueous mixture of gastric lipase, pepsin and one or more suitable gastric diluent components, at a pH from about 1.5 to about 3.5.

In a further embodiment, the MGS further comprises a salivary phase consisting essentially of synthetic saliva comprising an aqueous mixture of one or more salivary enzyme(s), and one or more suitable salivary diluent components at a pH in the range of from about 5 to 9, preferably from about 6.8 to 7.8.

In a further aspect the invention provides a model gut comprising: a salivary phase consisting essentially of synthetic saliva comprising an aqueous mixture of one or more suitable enzymes, and one or more suitable salivary diluent components at a pH in the range of from about 5 to 9; a gastric phase wherein the gastric phase comprises: consisting essentially of synthetic gastric juice comprising an aqueous mixture of gastric lipase, pepsin and one or more suitable gastric diluent components, at a pH from about 1.5 to about 3.5; and bile; and a pancreatic phase, a pancreatic phase consisting essentially of synthetic pancreatic juice comprising pancreatin and one or more suitable pancreatic diluent(s) at a pH from about 7 to about 9, preferably about 7.9 to about 8.2, and bile.

In each of the above models preferably the bile is porcine bile. Alternatively the bile is, bovine or ovine bile. More preferably the porcine bile is collected from porcine gall bladders. Alternatively the bile is a synthetic bile, bile acids, lecithinan, bilirubin or a combination thereof.

The pancreatin may be dialysed pancreatin, for example pancreatin dialysed through a semi-permeable membrane having a molecular weight Cut-off (MWCO) of from about 12,000 to about 14,000 Daltons. Preferably the dialysed pancreatin is provided at a concentration of 5-40 mg/ml, preferably 6.5-12 mg/ml, more preferably 9 mg/ml of pancreatic diluent. In a preferred embodiment, the pancreatin is added 0.1-2.5 ml/min, preferably at a rate of 0.5 ml/min. Accordingly dialysed pancreatin is preferably present in the pancreatic phase at a level of from about 0.1 to about 15,000 mg.

The pancreatin may be non-dialysed pancreatin. Preferably the non-dialysed pancreatin is provided at a concentration of 50-90 mg/ml pancreatin, preferably 70 mg/ml of pancreatic diluent. In a preferred embodiment, the pancreatin is added 0.1-2.5 ml/min, preferably at a rate of 0.5 ml/min. Accordingly non dialysed pancreatin is preferably present in the pancreatic phase at a level of from about 0.1 to about 30,000 mg.

Alternatively the pancreatin is synthetic pancreatin comprising amylase, trypsin, chymotrypsin, pancreatic lipase and elastase carboxypeptidase A or B.

In each of the above aspects preferably, the porcine bile is present at a level of from about 0.25 to 0.75 ml, preferably about 0.5 ml, per ml of pancreatic diluent.

In each of the above aspects preferably, the pancreatic diluent comprises $NaHCO_3$, $K_2HPO_4$, NaCl, $CaCl_2.2H_2O$, and urea. In a particularly preferred embodiment the pancreatic diluent comprises from about 82.5 to about 137.5 mM $CHNaO_3$, about 1.8 to about 3.1 mM $K_2HPO_4$, about 41.2 to about 68.6 mM NaCl, from about 0.75 to about 1.25 mM $CaCl_2.2H_2O$, and from about 1.25 to about 2.09 mM urea, preferably, titrated to about pH 7.5 to about 8.5. Most preferably, the pancreatic diluent comprises from about 110 mM $CHNaO_3$, 2.5 mM $K_2HPO_4$, 54.9 mM NaCl, 1 mM $CaCl_2.2H_2O$, and 1.67 mM urea titrated to about pH 8.

The level of NaHCO$_3$ in the pancreatic diluent may be varied such that, in use, the release of fatty acids from triglyceride analytes does not lower the pH to a non-physiological level in the pancreatic phase.

In each of the above aspects preferably, the pancreatic diluent further comprises mucin, for example porcine stomach mucin. More preferably the pancreatic diluent comprises mucin at a level of 1 mg/ml.

In each of the above aspects preferably, the synthetic pancreatic juice is filtered prior to use, for example using glass wool.

In each of the above aspects the models are preferably non-dynamic. As used here in the term non-dynamic refers to a model that recreates chemical and enzymatic conditions of digestion, in the absence of physical processes of digestion such as peristaltic motion, gastric motility and absorption.

In each of the above models preferably the gastric lipase is bacterial lipase, such as gastric lipase AP12 by Amano Enzymes, or alternatively a fungal lipase. Preferably, pepsin is porcine pepsin or alternatively a synthetic pepsin.

Preferably, synthetic gastric juice comprising an aqueous mixture of gastric lipase, pepsin and one or more suitable gastric diluent components, at a pH from about 1.5 to about 3.5

Preferably, the relative v/ml ratio of gastric lipase:porcine pepsin is from about 10 µg/ml:125 µg/ml to about 40 µg/ml:500 µg/ml, preferably about 40 µg/ml:0.5 mg/ml. Preferably, the gastric lipase is present at a level of from about 40 µg/ml of pancreatic diluent. Preferably, the pepsin is present at a level of from about 500 µg/ml of pancreatic diluent. In a preferred embodiment, the synthetic gastric juice is added to the gastric phase at a rate of 0.1-2.5 ml/min, preferably at a rate of 0.5 ml/min. Accordingly pepsin is preferably present in the gastric phase at a level of from about 85 to about 5000 µg/ml synthetic gastric juice. Accordingly lipase is preferably present in the gastric phase at a level of from about 8.5 to about 250 µg/ml synthetic gastric juice.

Preferably, the gastric diluent comprises NaCl, KCl, KH$_2$PO$_4$, and urea. In a particularly preferred embodiment the gastric diluent comprises from about 37 to about 61 mM NaCl, about 7.05 to about 11.75 mM KCl, about 1.5 to about 2.5 mM KH$_2$PO$_4$, from about 3.5 to about 6.25 mM urea. Most preferably, the gastric diluent comprises about 49.6 mM NaCl, about 9.4 mM KCl, about 2 mM KH$_2$PO$_4$, and about 5 mM urea titrated to pH 2.0.

Preferably, the synthetic gastric juice is present as a 20% to 80% aqueous solution. Preferably, the aqueous solution is a 1:1 solution with de-ionised water.

Preferably, the salivary diluent comprises NaHCO$_3$, K$_2$HPO$_4$.3H$_2$O, NaCl, KCl, and CaCl$_2$.2H$_2$O. In a particularly preferred embodiment the salivary diluent comprises from about 46.5 to about 77.5 mM NaHCO$_3$, about 4.5 to about 7.5 mM K$_2$HPO$_4$.3H$_2$O, about 11.25 to about 18.75 mM NaCl, about 4.69 to about 8.03 mM KCl, and about 2.25 to about 3.75 mM CaCl$_2$.2H$_2$O titrated to pH 7.4.

Preferably, the salivary enzyme is amylase, preferably α-amylase. Preferably, the amylase is present at a level of from about 0.01 µl/ml to about 2 µl/ml, preferably 1 (µl/ml of salivary diluent. Preferably, the synthetic saliva is present as a 20% to 80% aqueous solution. Preferably, the aqueous solution is a 1:1 solution with de-ionised water.

Preferably the Model Gut further comprises an analyte comprising carbohydrates, and/or lipids, and/or proteins, and or breakdown products thereof. For example, the analyte may be a foodstuff, a pharmaceutical or therapeutic product.

The aforementioned model systems are particularly useful for analysing carbohydrates, and/or triglycerides, and/or proteins or breakdown products thereof and samples isolated from the model systems, particularly samples comprising analyates, may be used with any assays known in the art for analysing carbohydrates, and/or triglycerides, and/or proteins or breakdown products thereof. Such assays include Zenbio Glycerol assay, Megazime K-Gluc assay and Pierce BCA Protein assay.

Preferably, the analyte is digested in the salivary phase from about 1 to 15 minutes, preferably about 10 minutes. Preferably, the analyte is digested in the gastric phase from about 30 to 120 minutes, preferably about 60 minutes. Preferably the analyte is digested in the pancreatic phase from about 45 to 240 minutes, preferably about 190 minutes.

Preferably, the analyte is transferred from the salivary phase to the gastric phase following digestion. Preferably the analyte is transferred from the gastric phase to the pancreatic phase following digestion. Preferably, the analyte is transferred from the salivary phase to the gastric phase following digestion in the salivary phase, followed by transfer from the gastric phase to the pancreatic phase following digestion in the gastric phase.

Preferably, the analyte is transferred from the gastric phase to the pancreatic phase in the synthetic pancreatic juice. Preferably, the analyte is transferred from the s salivary phase to the gastric phase in the synthetic saliva.

In a further aspect the invention provides a method of analysing carbohydrates, and/or triglycerides, and/or proteins from a mixed physiological sample comprising the steps of: treatment of a mixed physiological sample with trichloroacetic acid (TCA), optionally followed by centrifugation; treatment of the TCA-treated sample with potassium chloride (KCl), wherein the KCl treatment is present as an aqueous solvent solution; centrifugation of the resultant sample; and analysis of the breakdown products of carbohydrates, and/or lipids, and/or proteins present in the supernatant of the resultant sample.

As used herein, the term "mixed physiological sample" refers to a sample that comprises at lease one of the following components: A mixed physiological sample could include one or more of the following components: a diluent chemical, for example NaHCO$_3$, K$_2$HPO$_4$.3H$_2$O, NaCl, KCl; an enzyme, for example pepsin, amylase, lipase; bile, for example bile salts, lecithin bilirubin; mucus; and food substrates, for example carbohydrates, proteins, fats, indigestible fibre. Preferably, the mixed physiological sample includes one or more food substrates (for example carbohydrates, proteins, fats, indigestible fibre), one or more diluent chemical (for example NaHCO$_3$, K$_2$HPO$_4$.3H$_2$O, NaCl, KCl) and optionally, one or more of the following components salivary amylase, gastric lipase, pepsin, bile, pancreatin and/or mucous.

Preferably, the TCA is present in an amount effective for precipitation of undigested protein in the sample. Preferably, the TCA is present as a 5% to 20% aqueous solution and the ratio of sample volume to TCA solution volume is in the range of from about 1:0.5 to about 1:2.

Preferably, the KCl is present in an amount effective for precipitation carbohydrate in the sample. Preferably, KCl is present as at level of from about 1% to about 5% weight in a solvent solution comprising from 60% to about 80% aqueous organic solvent. Preferably, the ratio of sample volume to KCl solution volume is in the range of from about 1:5 to about 1:15. Preferably, the solvent is methanol (MeOH). Alternatively, the solvent may be a higher alcohol, for example propanol.

As referred to herein, the breakdown products of carbohydrates are monosaccharaides and/or short oligosaccharides, and/or the breakdown products of lipids are glycerol and/or fatty acids, and/or the breakdown product of proteins are amino acids and/or oligopeptides.

The method may further comprises centrifugation of the TCA treated sample, preferably at 10,000 rpm for 10 minutes, from about 12 hours to about 48 hours following treatment, preferably about 24 hours following treatment.

In a preferred embodiment the mixed physiological sample to be analysed is isolated from the MSI of the invention, for example an MGS to which an analyte has been added.

In one embodiment the MSI or MGS is automated, i.e. transfer of samples from the mouth to stomach and/or stomach to small intestine is automated. In another embodiment sampling of mixed physiological sample from the salivary, gastric and/or pancreatic phases is automated Experimental Methods Preparation of Synthetic GI Fluids Synthetic GI fluids are not specifically buffered, but have been designed to simulate the pH changes and ionic content of the GI tract. Fluids can be made up as stock solutions, enzymes are added fresh before each run. All chemicals and enzymes were purchased from Sigma-Aldrich unless otherwise stated.

Synthetic Saliva:

α-amylase (Sigma-Aldrich) was prepared at 1 µl/ml in Salivary Diluent (62 mM $NaHCO_3$, 6 mM $K_2HPO_4.3H_2O$, 15 mM NaCl, 6.43 mM KCl, 3 mM and $CaCl_2.2H_2O$, titrated to pH 7.4). Prior to running the assay, the mixture of salivary diluent and 1 µl/ml α-amylase was diluted 1:1 with deionised water to provide the synthetic saliva as utilised herein.

Synthetic Gastric Juice:

40 µg/ml of bacterial gastric lipase (Amano Enzyme Company) and 0.5 mg/ml porcine pepsin (Sigma-Aldrich) was prepared in Gastric Diluent (49.6 mM NaCl, 9.4 mM KCl, 2 mM $KH_2PO_4$ and, 5 mM urea, titrated to pH 2.0).

Synthetic Pancreatic Juice:

70 mg/ml of pancreatin (Sigma-Aldrich) was prepared in Pancreatic Diluent (110 mM $CHNaO_3$, 2.5 mM $K_2HPO_4$, 54.9 mM NaCl, 1 mM $CaCl_2.2H_2O$, 1.67 mM urea, and 1 g/l mucin titrated to pH 8) and filtered through glass wool. Fresh porcine bile was extracted from fresh procine gall bladders (collected on ice from abattoir). Approximately 50 gall bladders were collected per batch. The collected bile was pooled, mixed and frozen down in 25 ml aliquots for storage, as 25 ml is required for each replicate.

Substrate Preparation

All substrates, samples and controls are tested in triplicate. Protein, triglyceride and carbohydrate substrates can be tested separately, or in a mixed model, but are described here separately. Substrates mixes are made up to 10 ml with Synthetic Saliva as described below and incubated on rollers for 10 minutes before addition to the resting reservoir of gastric diluent.

Fat Digestion—

Six triglycerides of varying fatty acid chain lengths have been validated in the model gut system (Table 1). For validation of triglycerides which release fatty acids (FA's) with low pKa values (indicated * in Table 1) the pancreatic diluent was modified to 322.8 mM $NaHCO_3$ in order to counteract a lowering of pH as the FAs were released. Glyceryl trioctanoate was used as the tryglyceride substrate for all assays of fat digestion reported herein. In these experiments, 2 mmol (0.94136 g) of glyceryl trioctanoate was added to the synthetic saliva preparations at T[−10] wherein T[−10] means 10 minutes prior to addition of the synthetic saliva to the test system.

Table 1 illustrates the 6 triglyceride substrates tested, and the pKas of their constituent Fatty acids.

TABLE 1

| Triglyceride | Fatty Acid | pKa |
|---|---|---|
| Triacetin* | Acetic Acid | 4.5 |
| Glyceryl Tributyrate* | Butyric Acid | 4.84 |
| Glyceryl Trioctanoate* | Octanoic Acid (Caprylic acid) | 4.9 |
| Glyceryl Tripalmitate | Palmitic Acid | 9.7 |
| Glyceryl Trioleoate | Oleic Acid | 9.95 |
| Glyceryl Tristearate | Stearic Acid | 10.15 |

Carbohydrate Digestion:

Corn, wheat and potato starch in both native and gelatanised forms have been validated as carbohydrate substrates in the model gut system (MGS). Native Corn Starch has been used as the carbohydrate substrate for all assays of carbohydrate digestion reported herein. To investigate carbohydrate digestion, 1 g of Corn Starch was added to Synthetic Saliva Preparation at T[−10]

Protein Digestion:

In order to distinguish effects on protein digestion from the gastric and pancreatic phases of digestion, separate gastric and pancreatic proteolysis assays were carried Out.

Gastric Protein Digestion:

Bovine Serum Albumin (BSA) and Casein have both been validated as protein substrates in the model gut system. BSA was purchased from Fisher Scientific and has been used as the protein substrate for all assays of protein digestion reported herein. In the gastric phase 0.5 g BSA was added to the salivary diluents at T[−10] and the assay was run until the end of the gastric phase at T[60].

Small Intestinal Protein Digestion:

For assays of protein digestion in the small-intestinal phase, 1 g of BSA was added to Synthetic Saliva at T[−10] and gastric pepsin was omitted from the gastric diluent to prevent any protein digestion in the gastric phase.

Control and Test Sample Preparation

For background controls 10 ml Synthetic Saliva was prepared without substrate.

For sample testing substrate was prepared in accordance with the methodology for preparation of substrate control with known amounts of varying test samples added. For sample controls 10 ml synthetic saliva is prepared with appropriate amount of test sample, but without substrate.

For biopolymer testing 125, 250 and 500 mg of Biopolymer Sample was prepared with Synthetic Salivary Preparations. Acarbose, Orlistat, pentosan polysulphate and soybean trypsin inhibitor have all been used as positive inhibition controls for α-amylase, lipase, pepsin and trypsin respectively.

Inhibitors were prepared according to literature methods at appropriate concentrations to achieve inhibition.

Alginate and Fucoidan samples were provided by FMC Biopolymer. Alginate is an indigestible polysaccharide and as such can be considered a dietary fibre. Alginates are unbranched polysaccharides composed of (1-4)-α-L-guluronic acid (G-Residues) and (1-4)-β-D-mannuronic acid residues (M-Residues). The polyuronic chains are composed of blocks of about 20 residues which are either G-rich, M rich, or MG rich. The characteristics of the alginate are dictated by the arrangement of these blocks. Aginate has bioactive properties. Fucoidan is a highly sulphated polysaccharide extracted from brown seaweed (FMC Biopolymer).

Equipment

Synthetic GI fluids were pre-incubated at 37° C. in a water bath. Sample beakers (3×500 ml glass beakers) were prepared in a 37° C. water bath with overhead stirrers to simulate stomach churning. A Watson Marlow Peristaltic pump was set at 0.5 ml/min. A BioTek EL808 96 well plate spectrophotometer was used for sample analysis. The equipment set-up is illustrated in FIG. 1.

Sample Testing in the MGS

All substrates, samples and controls were tested in triplicate. Protein, triglyceride and carbohydrate substrates can be tested separately, or in a mixed model, and are described here separately.

Salivary Phase—

At T[−10], salivary preparations containing substrate/sample/controls were prepared as indicated hereinbefore and incubated for 10 minutes on rollers.

Gastric Phase—

At T[0] the salivary preparations were added to a resting reservoir of 50 ml synthetic gastric juice which had been pre-incubated to 37° C. in water bath with an overhead stirrer. Additional synthetic gastric juice (pre-incubated to 37° C.) was added immediately at a rate of 0.5 ml/min using a peristaltic pump. Due to the risk of pepsin auto-digestion, the gastric diluent was prepared immediately prior to running assay at T[−20].

Pancreatic Phase—

At T[60] 25 ml of fresh porcine bile was added, the pumping of synthetic gastric juice is stopped, and filtered synthetic pancreatic juice is pumped into the system at a rate of 0.5 ml/min. In the examples herein the small-intestinal phase is continued until T[180]. However our experiments have shown that this phase can be continued for longer. A schematic of the overall process for individual testing of protein, triglyceride and carbohydrate substrates is shown in FIG. 2 and a corresponding anatomical model of the process is shown in FIG. 26.

Figure 2:
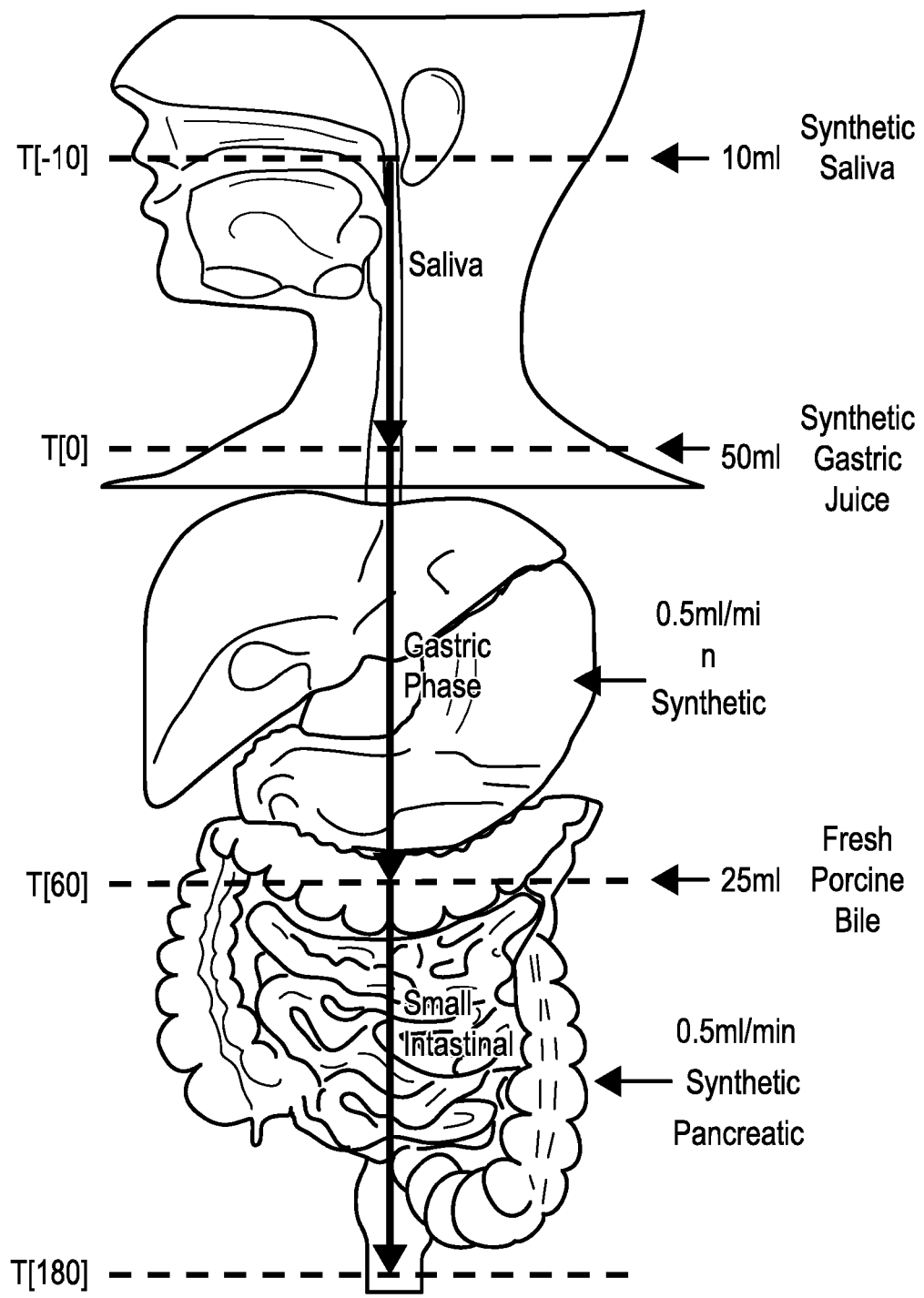
FIG. 2: Is a schematic of a model gut system (MGS) showing the addition of 10 ml of synthetic saliva at T[−10] in the salivary phase, 50 ml of synthetic gastric juice at T[0], followed by 0.5 ml/minute addition of synthetic gastric juice from T10 until the end of the gastric phase, in the salivary phase, 25 ml of fresh porcine bile at T[60], followed by 0.5 ml/minute addition of synthetic pancreatic juice from T[60] until the end of pancreatic phase.

FIG. 2: Illustrates the general procedure where a salivary preparation comprising a test sample (1a), or a control (1b), and substrate (3) are incubated for 10 minutes on rollers, from zero to 10 minutes, T−10 to T0, during the salivary phase [A], and then added to a resting reservoir containing an initial 50 ml Synthetic Gastric Juice (pre-incubated to 37° C. in water bath with overhead stirrer) at the start of the gastric phase [B]. During the gastric phase, from 0 to 60 minutes, T0 to T60, additional gastric juice is added at a rate of 0.5 ml/min with a peristaltic pump. At T60, 25 ml of Fresh Porcine Bile is added, corresponding to the start of the pancreatic phase [C] and the pumping of synthetic gastric juice is stopped, and filtered synthetic pancreatic juice is pumped in at a rate of 0.5 ml/min. In the current examples the small-intestinal phase is continued until 2 hours from the start ofg the salivary phase, T180.

Sampling

In all the experiments, data samples of 0.5 ml were taken at T0, T5, T10, T15, T30, T45, T60, T60$^B$, T65, T70, T75, T90, T105, T120, T150 and T180, wherein (T60$^B$) represents a second sample at T60 which was taken after the addition of fresh porcine bile. The test samples were immediately precipitated with 10% TCA (w/v) (trichloroacetic acid) at a ratio of 1:1. This step is included in order to stop enzyme activity and precipitate out undigested protein. The test samples were stored at 4° C. overnight to allow for precipitation and then centrifuged at 10,000 r.p.m. for 10 minutes, after which the supernatant was analysed. In calculating the test results, account is made for the dilution of the synthetic GI fluid volume, as well as for the sample dilution in TCA.

Analysis

Glycerol Analysis—

Triglyceride digestion can be measured using ZenBio Glycerol Reagent A to quantify the release of glycerol. A 5 μl of sample was incubated with 80 μl Reagent A for 30 minutes and colour development was measured at 550 nm. A standard curve was prepared from stock 2.5 mM glycerol solution.

Starch Analysis—

In order to separate maltase products of digestion from undigested starch substrate, 50 μl of supernatant was mixed with 950 μl of 1% KCl (w/v) 75% Methanol solution (v/v) and after 20 minutes was centrifuged at 10 k rpm for 10 minutes. 500 μl of the resulting supernatant was then evaporated down to a volume of 100 μl. Once cooled to 37° C., 50 μl of 1 mg/ml alpha glucasidase (Sorachim) was added and incubated at 37° C. for 2 hours. Liberated glucose was then assayed using the Megazyme D-Glucose (glucose oxidase/peroxidase; GOPOD) Assay Kit.

Proteolysis Analysis—

Undigested polypeptides were substantially removed from samples by TCA precipitation and centrifugation. Protein digestion can be measured by assaying amino acids and short oligopeptides remaining in the supernatant with the Pierce BCA Total Protein assay kit. Working Reagent (WR) was prepared by mixing Reagent A and Reagent B at ratio 50:1. A 25 μl of sample was incubated with 200 μl WR at 37° C. for 30 minutes and colour development measured at 575 nm. A standard curve was prepared using a stock solution of BSA at 2 mg/ml.

Experimental Results

The results of the control and test experiments are illustrated in FIGS. 3 to 25.

Discussion of Experimental Results

Figure 3:
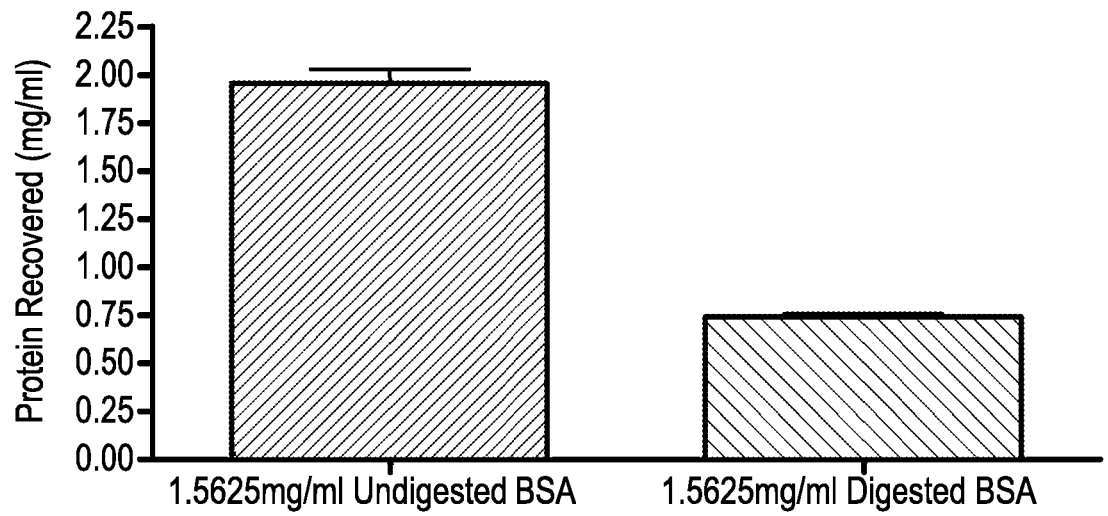
FIG. 3: Is a bar chart illustrating the relative amounts of undigested BSA versus digested BSA as measured using the Pierce BCA Total Protein assay kit, and in particular compares BCA reporting of 1.5625 mg of BSA before and after a 2-step pepsin/trypsin digestion.

FIG. 3: Illustrates in graphical format the results obtained from assaying amino acids and short oligopeptides remaining in the supernatant with the Pierce BCA Total Protein assay kit. To prepare the assay samples, undigested polypeptides are removed from samples by TCA precipitation and centrifugation. Working Reagent (WR) was prepared by mixing Reagent A and Reagent B at ratio 50:1. 25 ul of sample was incubated with 200 ul WR at 37° C. for 30 minutes and colour development measured at 575 nm. A standard curve is prepared using a stock solution of BSA at 2 mg/ml. FIG. 3 shows that only 37.76% of BSA is reported in this BCA assay after complete proteolysis. This can be corrected for by multiplying results by a factor of 2.648.

Figure 4:
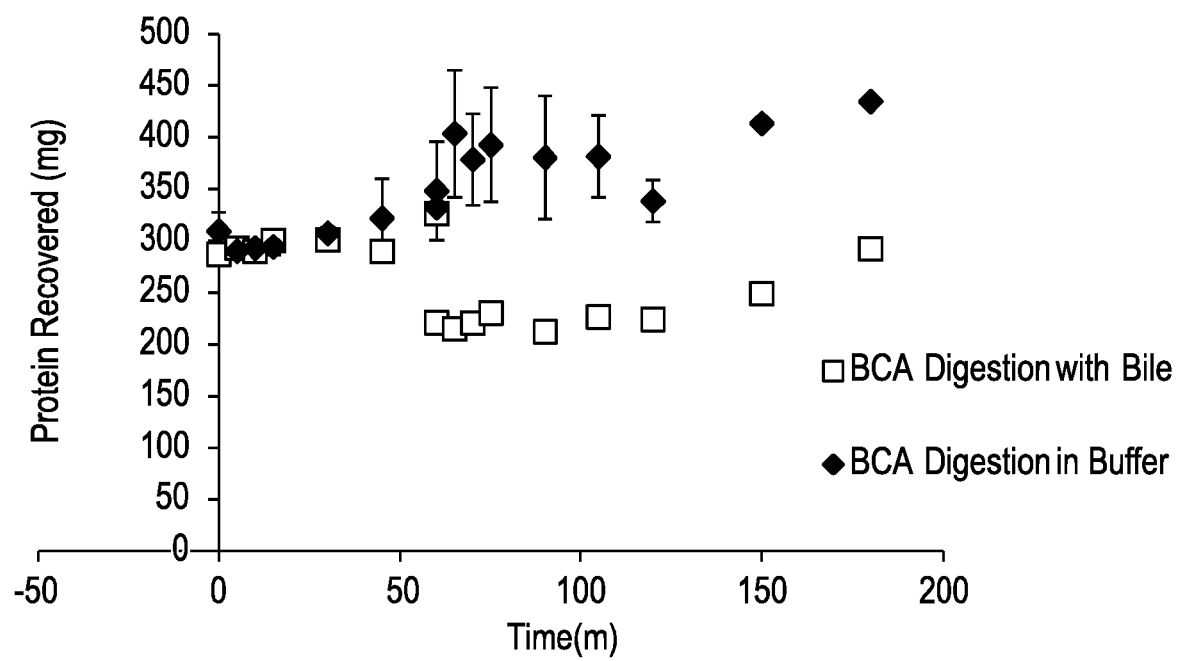
FIG. 4: Illustrates the detection of constant, known amount of digested protein in the model gut system (MGS), with and without bile.
Figure 5:
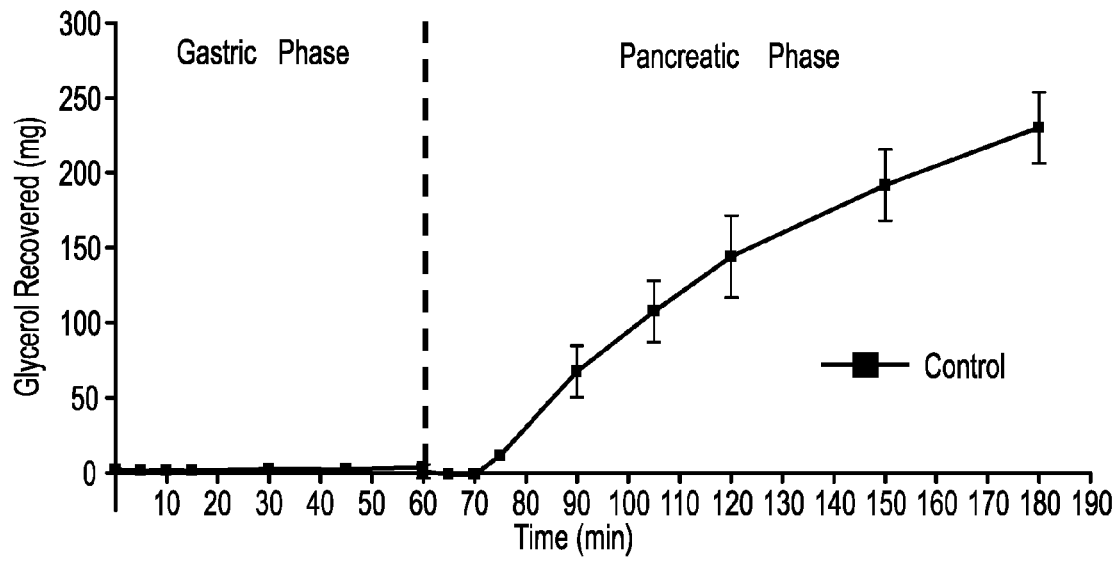
FIG. 5: Shows a control digestion of glyceryl trioctanoate in the model gut system (MGS)

FIG. 4: Shows that in the pancreatic phase of the MGS, from T60 to T180 minutes, only 60.325% of digested protein is detected. Digestion in bile is represented by (▧) and digestion in buffer is represented by (♦). Whilst not wishing to be bound to any particular theory it is proposed herein that this low detection is due to bile binding of protein metabolites. To account for this bile binding, and the under-reporting from the Assay discussed in FIG. 3, the Applicants multiply data from analysis of protein digestion in the small intestinal phase by a factor of 6.675 in order to correct for these factors. FIG. 5: Illustrates the results obtained for a controlled digestion of glyceryl trioctanoate in the model gut system (MGS) wherein T[0] represents the start of the gastric phase of digestion. 2 mmol of glyceryl trioctanoate was digested (Control Digestion). The graph shows total glycerol recovered from model gut system after TCA (trichloroacetic acid) precipitation to stop enzyme activity. Control digestion is represented as (■). All samples were tested in triplicate, and errors are shown as standard deviation. As previously shown in FIG. 4 no significant release of glycerol occurred during the salivary phase, prior to addition to the resting gastric reservoir. Similarly, FIG. 5 shows that throughout the gastric phase, from T(10) to T(60) there was similarly no release of glycerol. This data suggests that Gastric Lipase has little or no activity towards glycerol trioctanoate. Once the system enters the pancreatic phase beyond T(60) glycerol begins to be released from glyceryl trioctanoate.

Figure 6:
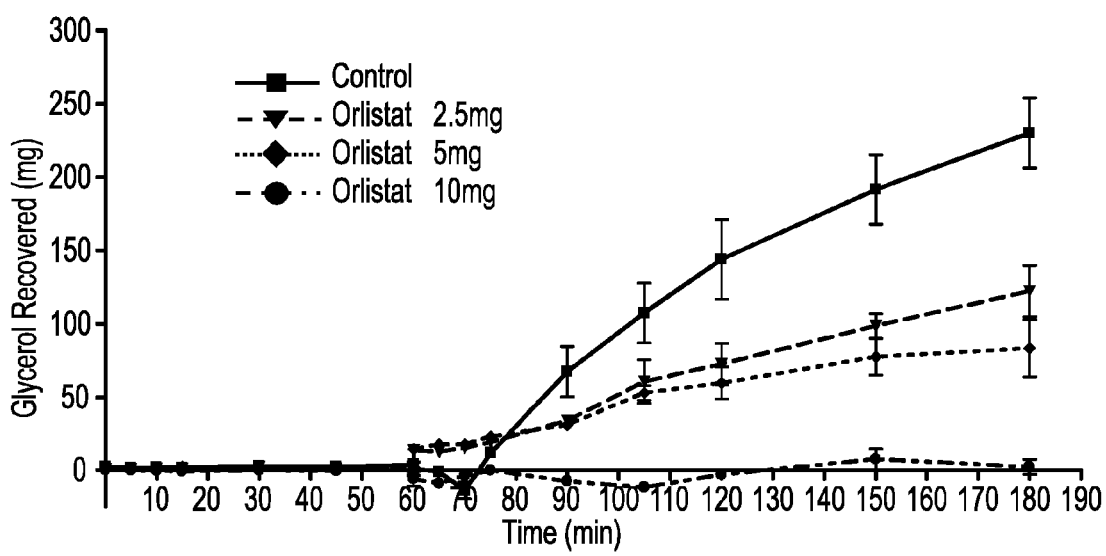
FIG. 6: Is a graph showing the digestion of glyceryl trioctanoate in the model gut system (MGS) with and without Orlistat®.

FIG. 6: Illustrates that for glyceryl trioctanoate digestion in a model gut system (MGS), that the total glycerol recovered from the model gut system (MGS) after TCA (trichloroacetic acid) precipitation to stop enzyme activity varies in accordance with the level of Orlistat® present. In these experiments, 2 mmol of glyceryl trioctanoate was digested alone as a Control digestion, and also in the presence of varying concentrations of Orlistat. Control digestion is represented as (■) and digestion with Orlistat at 2.5 mg as (▲), 5 mg (▼) and 10 mg (●) respectively. All samples were tested in triplicate and errors are shown as standard deviation.

Figure 7:
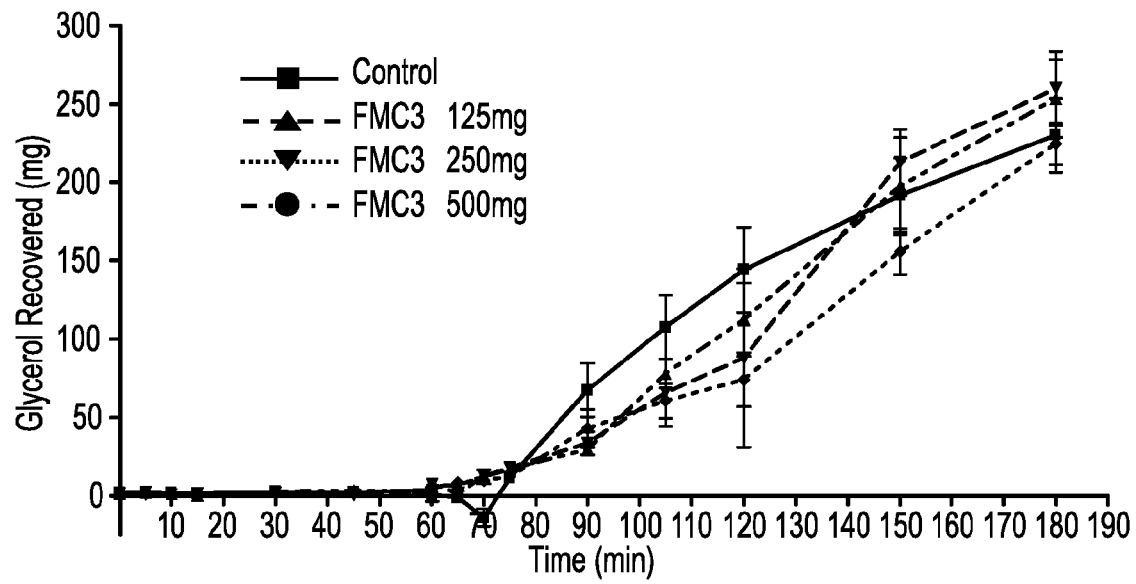
FIG. 7: Is a graph showing the digestion of glyceryl trioctanoate in the model gut system (MGS) with and without FMC3.

FIG. 7: Illustrates that for glyceryl trioctanoate digestion in a model gut system with and without FMC3, the total glycerol recovered from the model gut system (MGS) after TCA (trichloroacetic acid) precipitation to stop enzyme activity increases with the lever of FMC3 added. 2 mmol of glyceryl trioctanoate was digested alone to simulate Control digestion, also in the presence of varying concentrations of FMC3. Control digestion is represented as (■) and digestion with FMC3 at 125 mg as (▲), 250 mg (▼) and 500 mg (●). All samples were tested in triplicate, and errors are shown as standard deviation.

Figure 8:
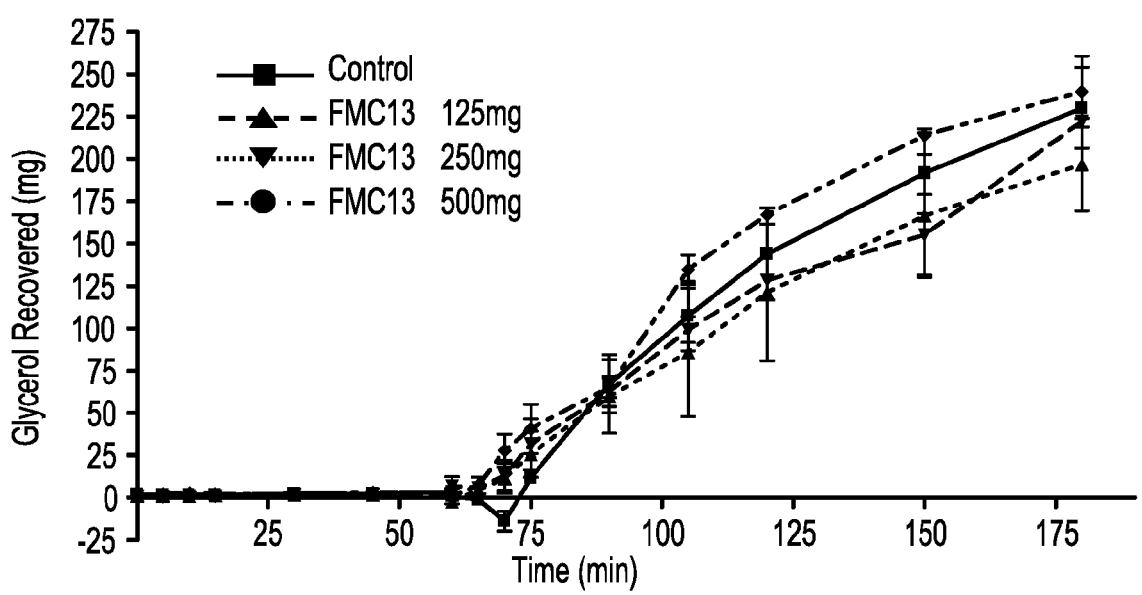
FIG. 8: Is a graph showing the digestion of glyceryl trioctanoate digestion in a model gut system (MGS) with and without FMC13.

FIG. 8: Illustrates that the total level of glycerol recovered from model gut system (MGS) after TCA (trichloroacetic acid) precipitation to stop enzyme activity varies in relation to the level of FMC13 and also in relation to the length of digestion time. In these experiments 2 mmol of glyceryl trioctanoate was digested alone as a simulation of Control digestion, as well as in the presence of varying concentrations of FMC13. Control digestion is represented as (■) and digestion with FMC13 at 125 mg as (▲), 250 mg (▼) and 500 mg (●). All samples were tested in triplicate, and the errors are shown as standard deviation.

Figure 9:
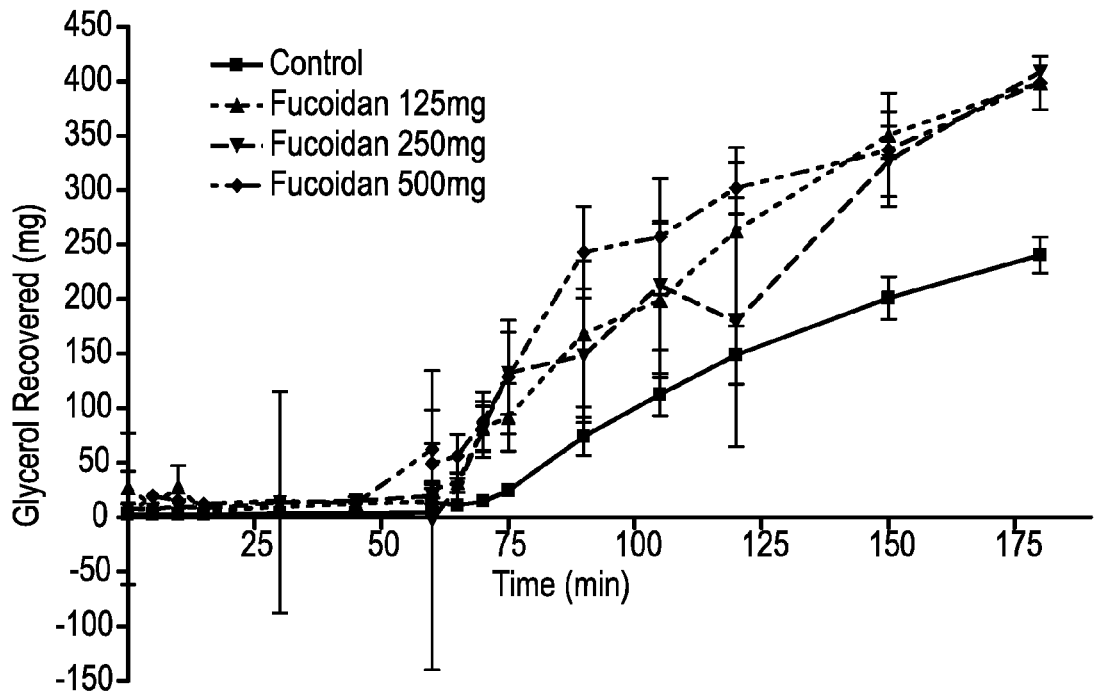
FIG. 9: Is a graph showing the digestion of glyceryl trioctanoate digestion in a model gut system (MGS) with and without Fucoidan.

FIG. 9: Illustrates that the total level of glycerol recovered from model gut system (MGS) after TCA (trichloroacetic acid) precipitation to stop enzyme activity varies in relation to the level of Fucoidan and also in relation to the length of digestion time. In these experiments 2 mmol of glyceryl trioctanoate was digested alone as a simulation of Control digestion, as well as in the presence of varying concentrations of Fucoidan. Control digestion is represented as (■) and digestion with Fucoidan at 125 mg as (▲), 250 mg (▼) and 500 mg (●). All samples were tested in triplicate, and the errors are shown as standard deviation.

Figure 10:
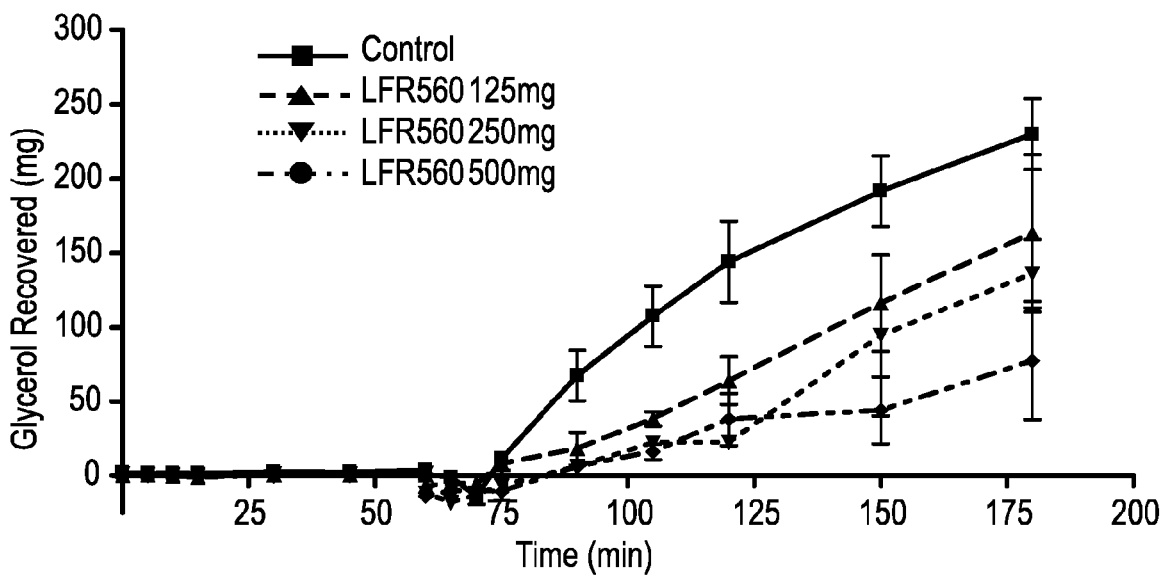
FIG. 10: Is a graph showing the digestion of glyceryl trioctanoate digestion in a model gut system (MGS) with and without LFR560.

FIG. 10: Illustrates that the total level of glycerol recovered from model gut system (MGS) after TCA (trichloroacetic acid) precipitation to stop enzyme activity varies in relation to the level of LFR560 and also in relation to the length of digestion time. In these experiments 2 mmol of glyceryl trioctanoate was digested alone as a simulation of Control digestion, as well as in the presence of varying concentrations of LFR560. Control digestion is represented as (■) and digestion with LFR560 at 125 mg as (▲), 250 mg (▼) and 500 mg (●). All samples were tested in triplicate, and the errors are shown as standard deviation.

Figure 11:
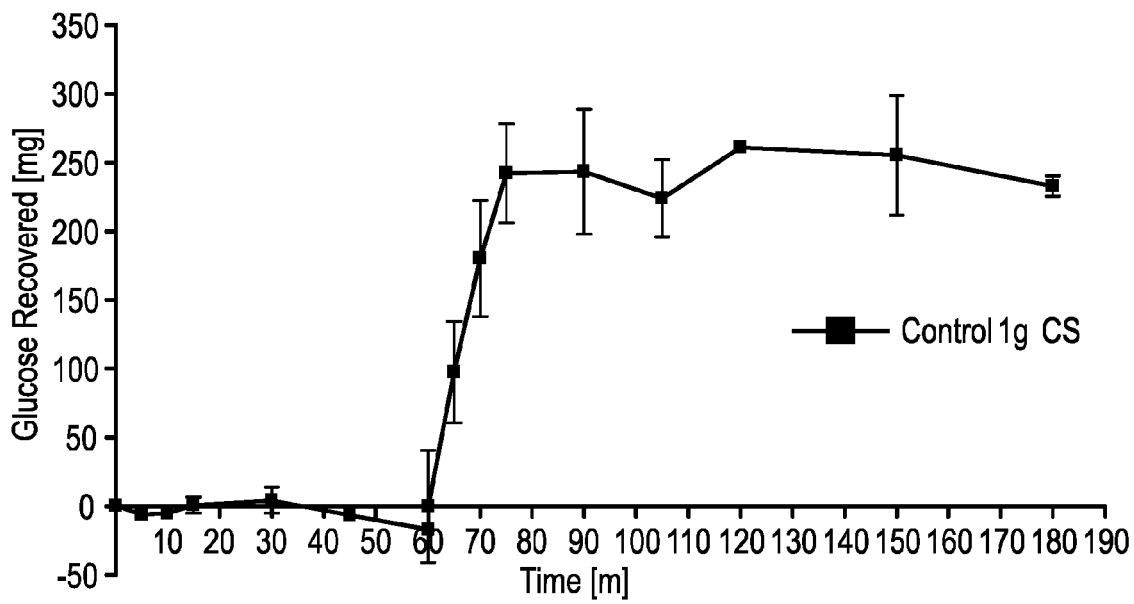
FIG. 11: Is a graph showing the digestion of corn starch digestion in a model gut system (MGS)

FIG. 11: Illustrates the total level of glycerol recovered from the model gut system (MGS) after TCA (trichloroacetic acid) precipitation to stop enzyme activity and methanol-KCl precipitation to remove undigested starch increases over time. In these experiments 1 g of native corn starch was digested alone as a simulation of Control digestion, and is represented as (■). All samples were tested in triplicate, and the errors are shown as standard deviation.

Figure 12:
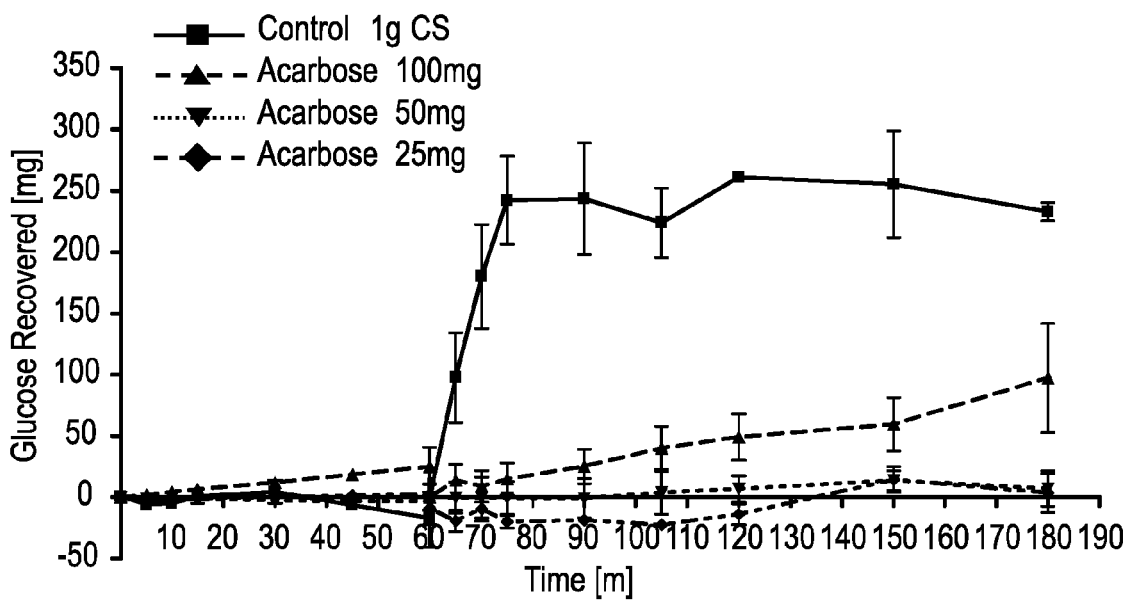
FIG. 12: Is a graph showing the digestion of corn starch digestion in a model gut system (MGS) with and without Acarabose.

FIG. 12: Illustrates that total level of glucose recovered from the model gut system (MGS) after TCA (trichloroacetic acid) precipitation to stop enzyme activity and methanol-KCl precipitation to remove undigested starch. In these experiments 1 g of native corn starch was digested alone as a simulation of Control digestion, is represented by (■) as well as in the presence of Acarbose at 100 mg as (▲), 50 mg (▼), and 25 mg (●). All samples were tested in triplicate, and the errors are shown as standard deviation.

Figure 13:
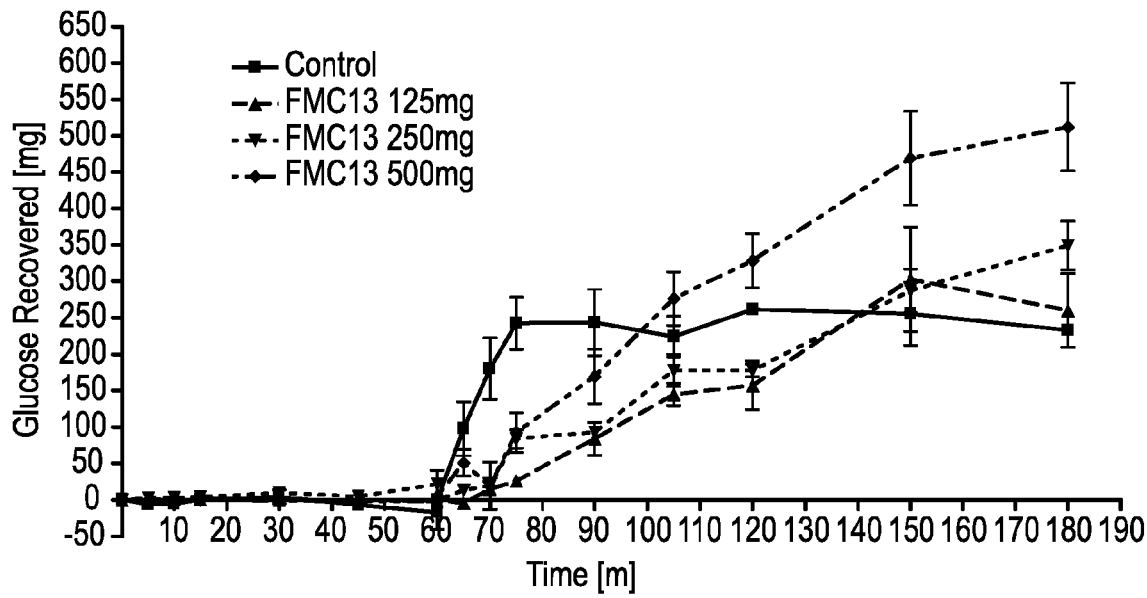
FIG. 13: Is a graph showing the digestion of corn starch digestion in a model gut system (MGS) with and without FMC13 Alginate.

FIG. 13: Illustrates that total level of glucose recovered from the model gut system (MGS) after TCA (trichloroacetic acid) precipitation to stop enzyme activity and methanol-KCl precipitation to remove undigested starch. In these experiments 1 g of native corn starch was digested alone as a simulation of Control digestion, is represented by (■) as well as in the presence of varying concentrations of FMC13 Alginate at 125 mg as (▲), 250 mg (▼), and 500 mg (●). All samples were tested in triplicate, and the errors are shown as standard deviation.

Figure 14:
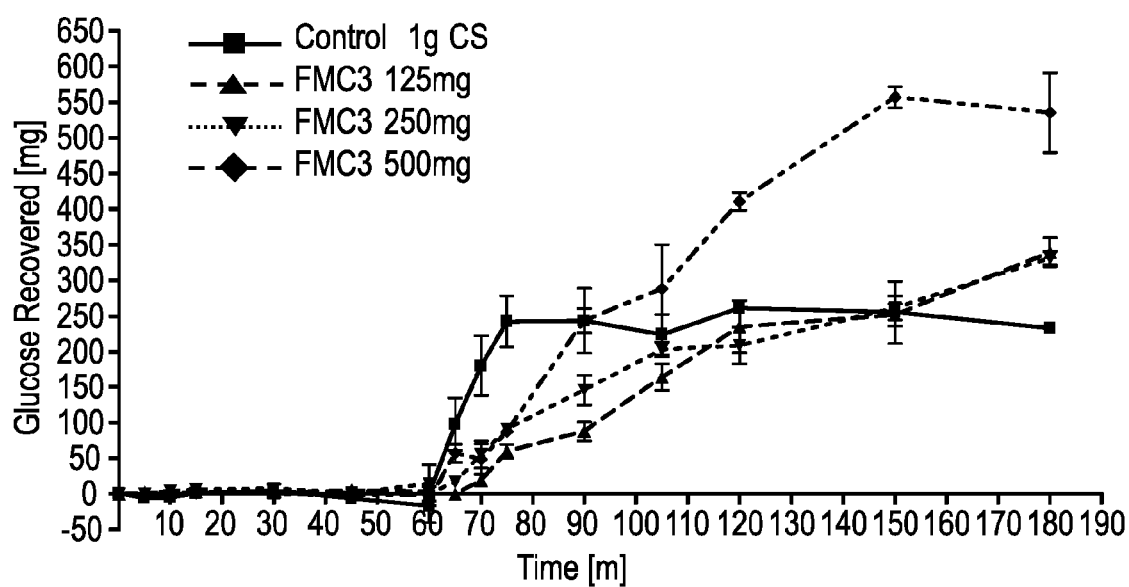
FIG. 14: Is a graph showing the digestion of corn starch digestion in a model gut system (MGS) with and without FMC3 Alginate.

FIG. 14: Illustrates that total level of glucose recovered from the model gut system (MGS) after TCA (trichloroacetic acid) precipitation to stop enzyme activity and methanol-KCl precipitation to remove undigested starch. In these experiments 1 g of native corn starch was digested alone as a simulation of Control digestion, is represented by (■) as well as in the presence of varying concentrations of FMC3 Alginate at 125 mg as (▲), 250 mg (▼), and 500 mg (●). All samples were tested in triplicate, and the errors are shown as standard deviation.

Figure 15:
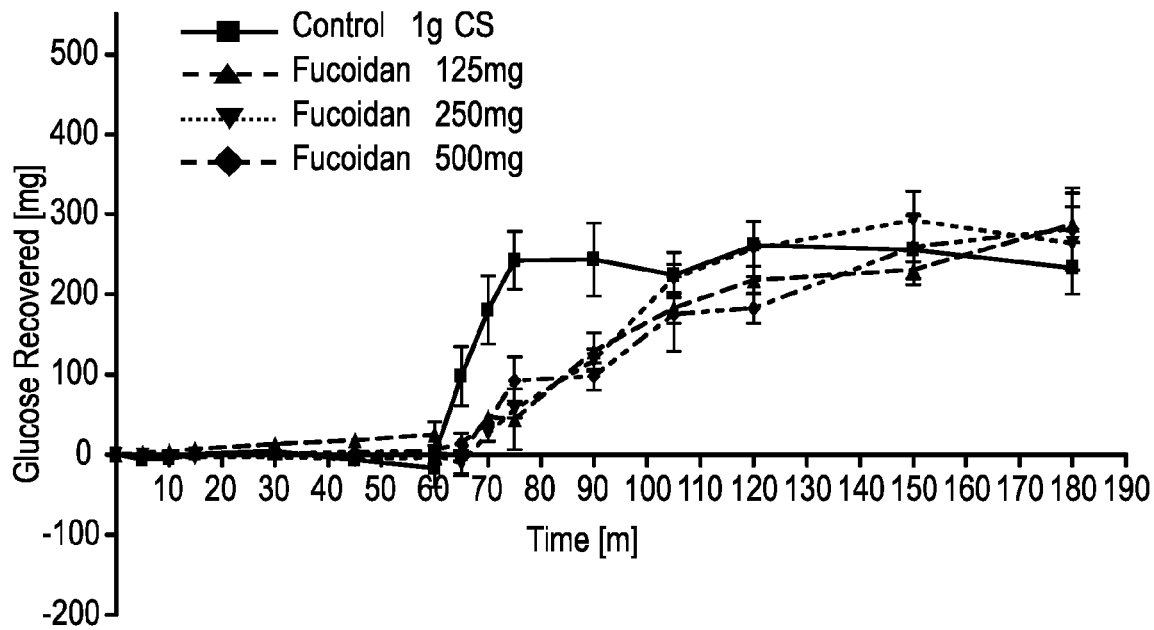
FIG. 15: Is a graph showing the digestion of corn starch digestion in a model gut system (MGS) with and without Fucoidan.

FIG. 15: Illustrates that total level of glucose recovered from the model gut system (MGS) after TCA (trichloroacetic acid) precipitation to stop enzyme activity and methanol-KCl precipitation to remove undigested starch. In these experiments 1 g of native corn starch was digested alone as a simulation of Control digestion, is represented by (■) as well as in the presence of varying concentrations of Fucoidan at 125 mg as (▲), 250 mg (▼), and 500 mg (●). All samples were tested in triplicate, and the errors are shown as standard deviation.

Figure 16:
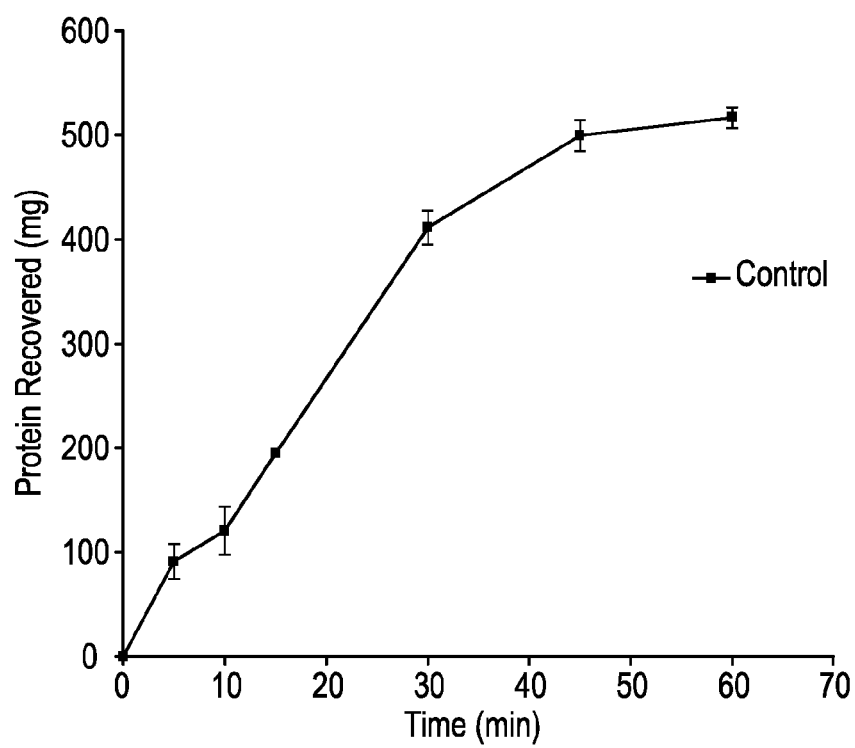
FIG. 16: Is a graph showing the digestion of bovine serum albumin (BSA) in the gastric phase (stomach) of a model gut system (MGS)

FIG. 16: Illustrates that total level of protein recovered from the model gut system (MGS) after TCA (trichloroacetic acid) precipitation to stop enzyme activity and remove undigested polypeptides. In these experiments 0.5 g BSA was digested alone as a simulation of Control digestion, and is represented by (■). All samples were tested in triplicate, and the errors are shown as standard deviation.

Figure 17:
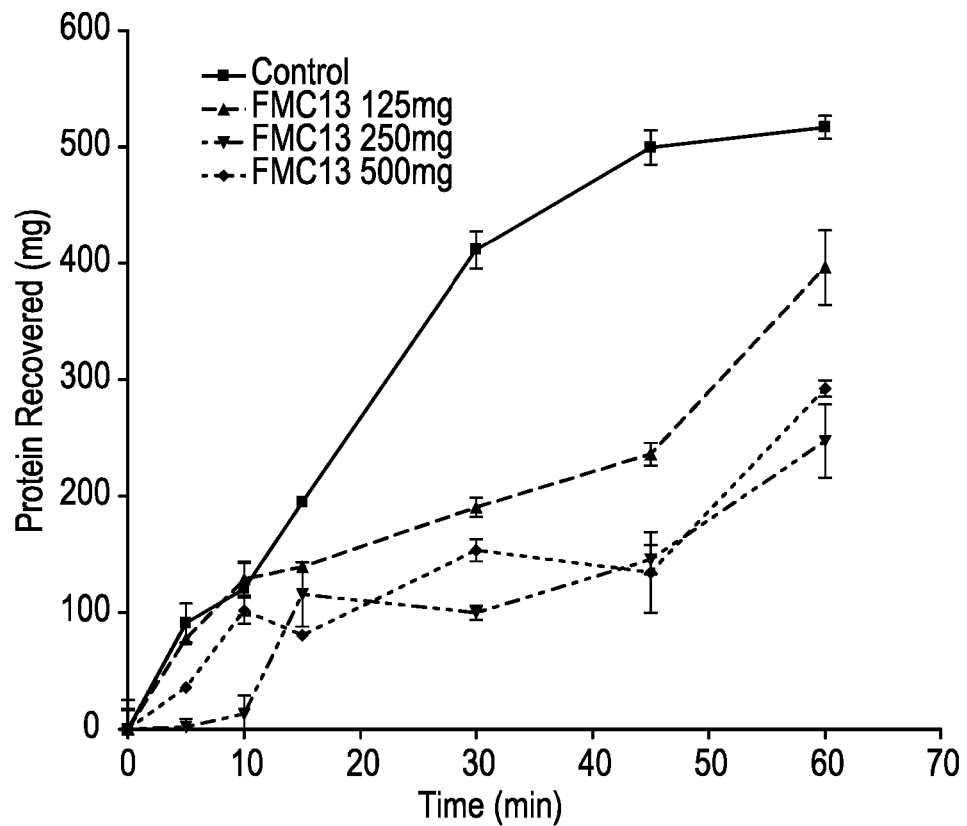
FIG. 17: Is a graph showing the digestion of bovine serum albumin (BSA) in the gastric phase (stomach) of a model gut system (MGS) with and without FMC13 Alginate.

FIG. 17: Illustrates that total level of protein recovered from the model gut system (MGS) after TCA (trichloroacetic acid) precipitation to stop enzyme activity and remove undigested polypeptides. In these experiments 0.5 g BSA was digested alone as a simulation of Control digestion, and in the presence of varying concentrations of FMC13 Alginate. Control digestion is represented as (■) and digestion with FMC13 Alginate at 125 mg as (▲), 250 mg (▼) and 500 mg as (●). All samples were tested in triplicate, and the errors are shown as standard deviation.

Figure 18:
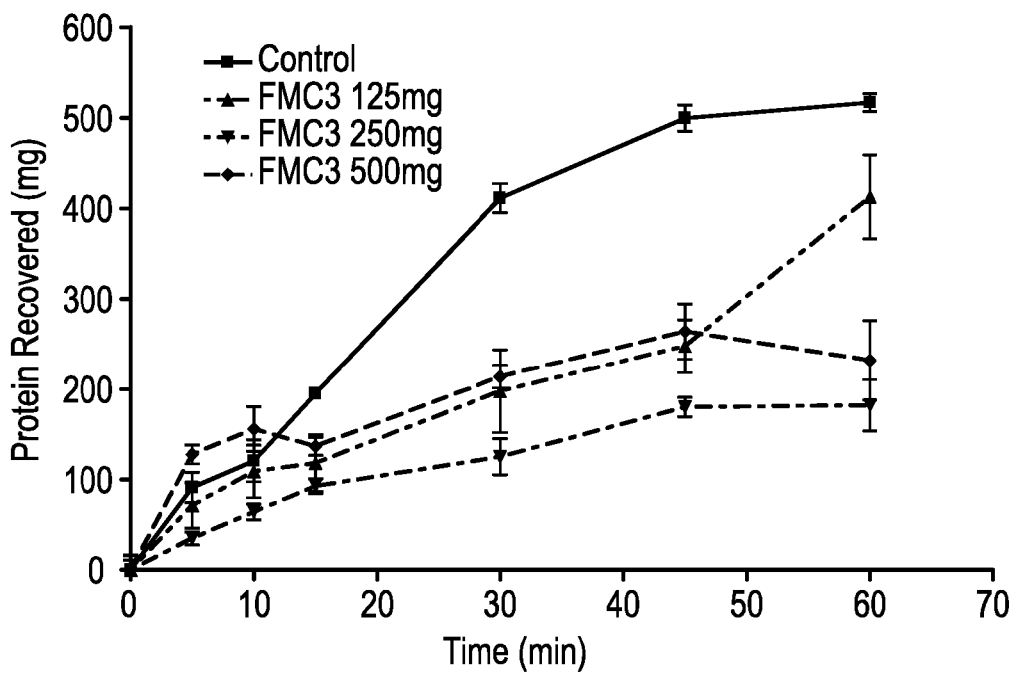
FIG. 18: Is a graph showing the digestion of bovine serum albumin (BSA) in the gastric phase (stomach) of a model gut system (MGS) with and without FMC3 Alginate.

FIG. 18: Illustrates that total level of protein recovered from the model gut system (MGS) after TCA (trichloroacetic acid) precipitation to stop enzyme activity and remove undigested polypeptides. In these experiments 0.5 g BSA was digested alone as a simulation of Control digestion, and in the presence of varying concentrations of FMC3 Alginate. Control digestion is represented as (■) and digestion with FMC3 Alginate at 125 mg as (▲), 250 mg as (▼) and 500 mg as (●). All samples were tested in triplicate, and the errors are shown as standard deviation.

Figure 19:
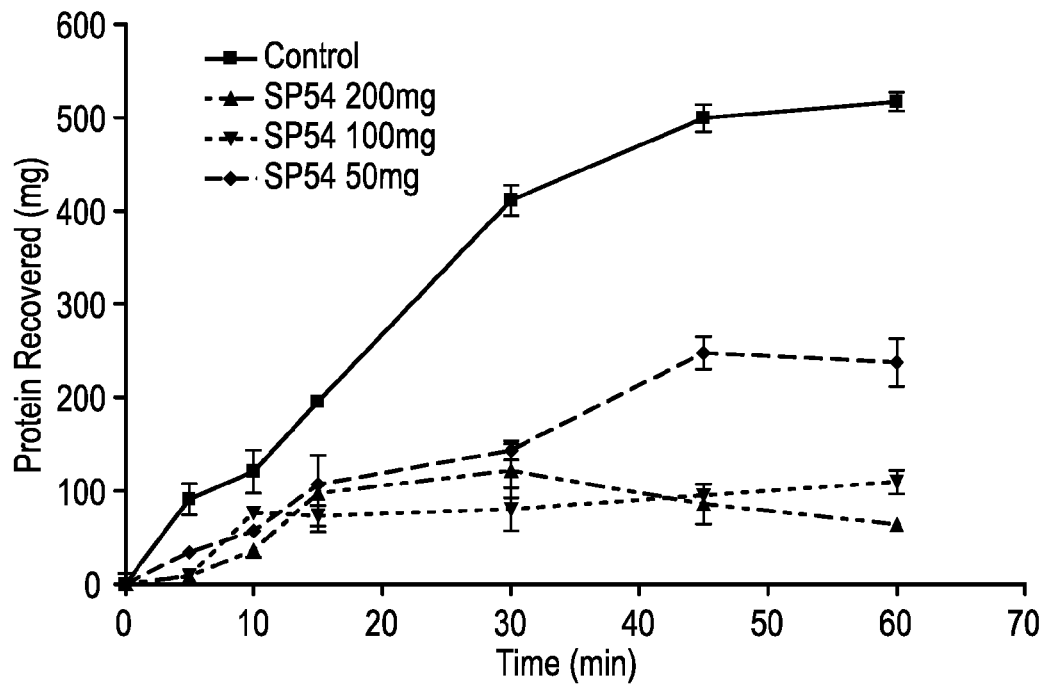
FIG. 19: Is a graph showing the digestion of bovine serum albumin (BSA) in the gastric phase (stomach) of a model gut system (MGS) with and without SP54.

FIG. 19: Illustrates that total level of protein recovered from the model gut system (MGS) after TCA (trichloroacetic acid) precipitation to stop enzyme activity and remove undigested polypeptides. In these experiments 0.5 g BSA was digested alone as a simulation of Control digestion, and in the presence of varying concentrations of SP54. Control digestion is represented as (■) and digestion with SP54 at 200 mg as (▲), 100 mg as (▼), 50 mg as (●) and 10 mg as (●). All samples were tested in triplicate, and the errors are shown as standard deviation.

Figure 20:
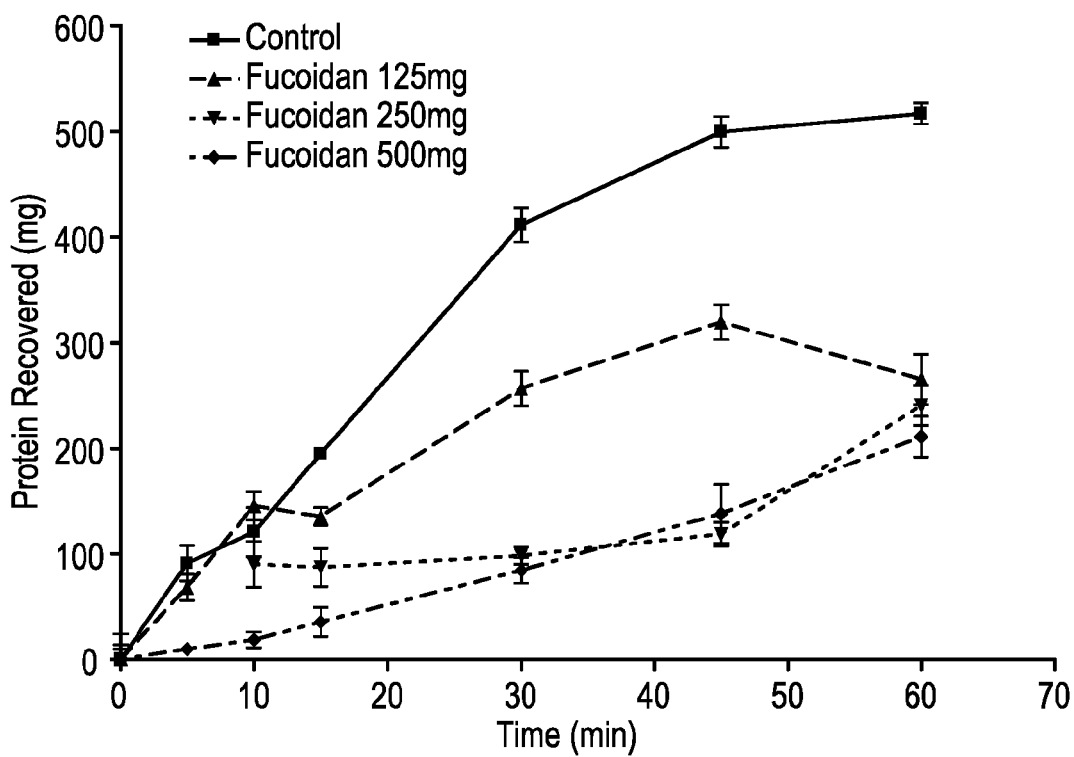
FIG. 20: Is a graph showing the digestion of bovine serum albumin (BSA) in the gastric phase (stomach) of a model gut system (MGS) with and without Fucoidan.

FIG. 20: Illustrates that total level of protein recovered from the model gut system (MGS) after TCA (trichloroacetic acid) precipitation to stop enzyme activity and remove undigested polypeptides. In these experiments 0.5 g BSA was digested alone as a simulation of Control digestion, and in the presence of varying concentrations of Fucoidan. Control digestion is represented as (■) and digestion with Fucoidan at 125 mg as (▲), 250 mg as (▼), and 500 mg as (●). All samples were tested in triplicate, and the errors are shown as standard deviation.

Figure 21:
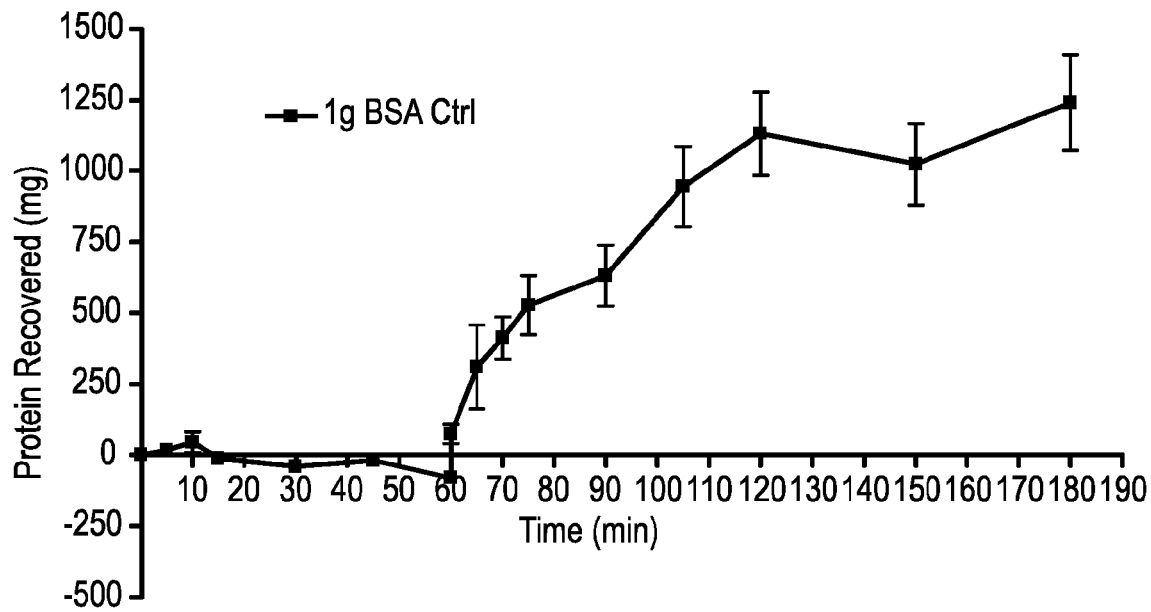
FIG. 21: Is a graph showing the digestion of bovine serum albumin (BSA) in the pancreatic/intestinal phase of a model gut system (MGS)

FIG. 21: Illustrates that total level of protein recovered from the model gut system (MGS) after TCA (trichloroacetic acid) precipitation to stop enzyme activity and remove undigested polypeptides. In these experiments 1 g BSA was digested alone as a simulation of Control digestion, and is represented as (■). All samples were tested in triplicate, and the errors are shown as standard deviation.

Figure 22:
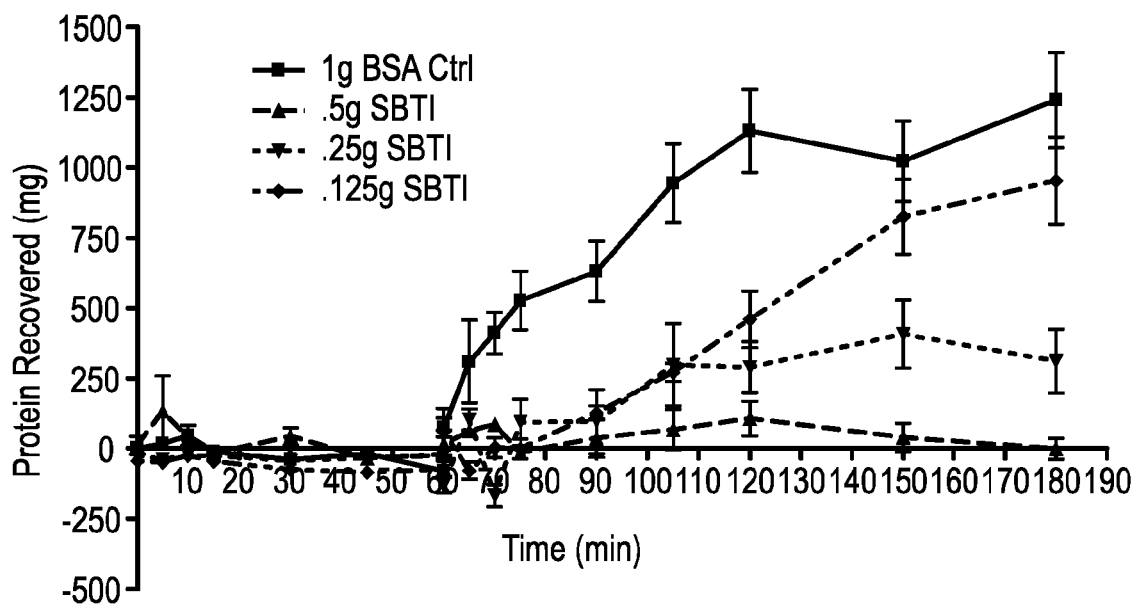
FIG. 22: Is a graph showing the digestion of bovine serum albumin (BSA) in the pancreatic/intestinal phase of a model gut system (MGS) with and without SBTI.

FIG. 22: Illustrates that total level of protein recovered from the model gut system (MGS) after TCA (trichloroacetic acid) precipitation to stop enzyme activity and remove undigested polypeptides. In these experiments 1 g BSA was digested alone as a simulation of Control digestion, and in the presence of varying concentrations of SBTI. Control digestion is represented as (■) and digestion with SBTI at 5 mg as (▲), 25 mg as (▼), and 125 mg as (●). All samples were tested in triplicate, and the errors are shown as standard deviation.

Figure 23:
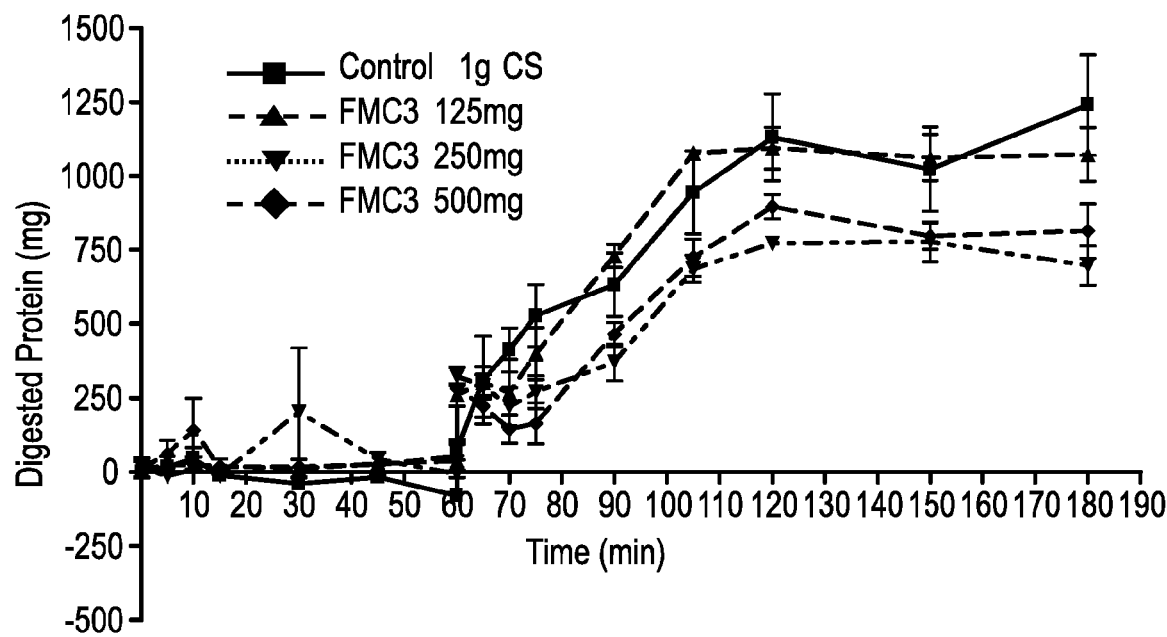
FIG. 23: Is a graph showing the digestion of bovine serum albumin (BSA) in the pancreatic/intestinal phase of a model gut system (MGS) with and without FMC3.

FIG. 23: Illustrates that total level of protein recovered from the model gut system (MGS) after TCA (trichloroacetic acid) precipitation to stop enzyme activity and remove undigested polypeptides. In these experiments 1 g BSA was digested alone as a simulation of Control digestion, and in the presence of varying concentrations of FMC3. Control digestion is represented as (■) and digestion with FMC3 at 125 mg as (▲), 250 mg as (▼), and 500 mg as (●). All samples were tested in triplicate, and the errors are shown as standard deviation.

Figure 24:
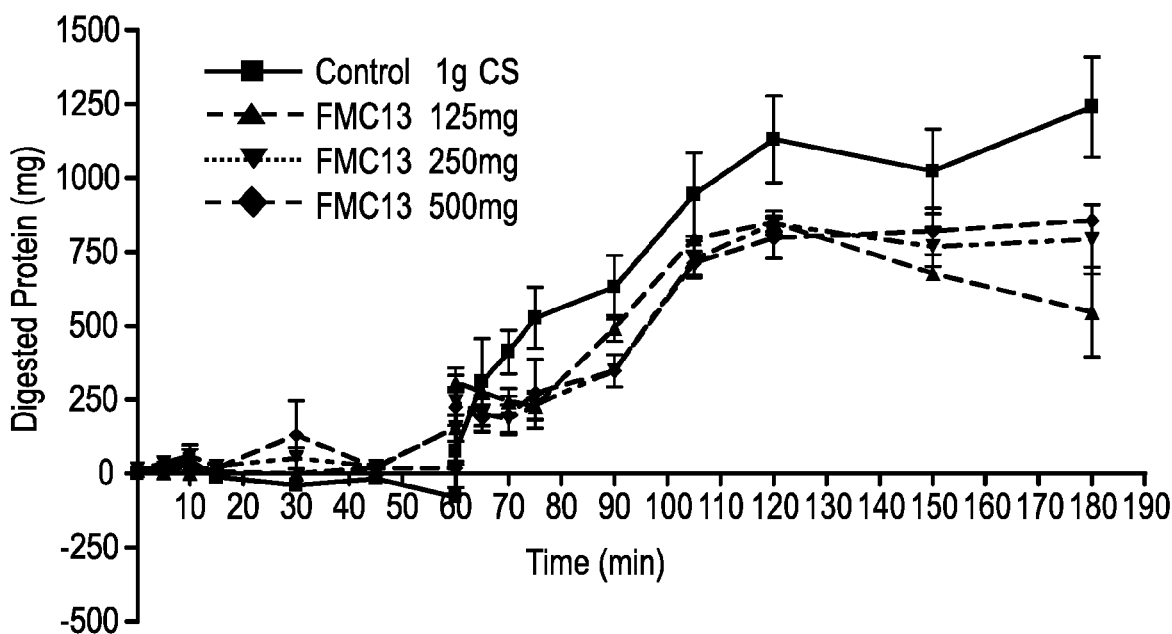
FIG. 24: Is a graph showing the digestion of bovine serum albumin (BSA) in the pancreatic/intestinal phase of a model gut system (MGS) with and without FMC13.

FIG. 24: Illustrates that total level of protein recovered from the model gut system (MGS) after TCA (trichloroacetic acid) precipitation to stop enzyme activity and remove undigested polypeptides. In these experiments 1 g BSA was digested alone as a simulation of Control digestion, and in the presence of varying concentrations of FMC13. Control digestion is represented as (■) and digestion with FMC13 at 125 mg as (▲), 250 mg as (▼), and 500 mg as (●). All samples were tested in triplicate, and the errors are shown as standard deviation.

Figure 25:
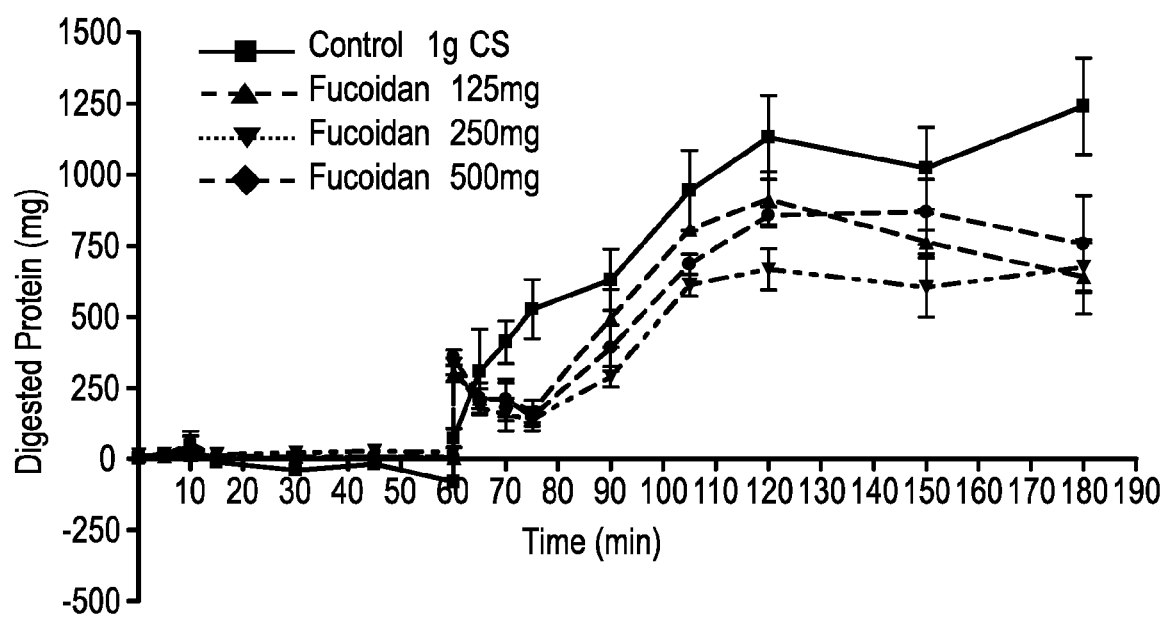
FIG. 25: Is a graph showing the digestion of bovine serum albumin (BSA) in the pancreatic/intestinal phase of a model gut system (MGS) with and without Fucoidan.

FIG. 25: Illustrates that total level of protein recovered from the model gut system (MGS) after TCA (trichloroacetic acid) precipitation to stop enzyme activity and remove undigested polypeptides. In these experiments 1 g BSA was digested alone as a simulation of Control digestion, and in the presence of varying concentrations of Fucoidan. Control digestion is represented as (■) and digestion with Fucoidan at 125 mg as (▲), 250 mg as (▼), and 500 mg as (●). All samples were tested in triplicate, and the errors are shown as standard deviation.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An method for analysing carbohydrates, and/or triglycerides, and/or proteins, and/or lipids, or breakdown products thereof; or for simulating digestion of an edible/potable substance, the method comprising:

(a) subjecting the carbohydrate, triglyceride, protein lipid, break down product or edible/potable substance to a salivary phase consisting essentially of synthetic saliva comprising an aqueous mixture of one or more salivary enzyme(s), and one or more suitable salivary diluent components at a pH in the range of from about 5 to 9;

(b) subjecting the product of (a) to a gastric phase consisting essentially of synthetic gastric juice comprising an aqueous mixture of gastric lipase, pepsin and one or more suitable gastric diluent components, at a pH from about 1.5 to about 3.5, wherein the synthetic gastric juice is added to the gastric phase at a rate of 0.1-2.5 ml/min; and (c) subjecting the product of (b) to a pancreatic phase consisting essentially of synthetic pancreatic juice comprising pancreatin and one or more suitable pancreatic diluent(s) at a pH from about 7 to about 9, and porcine bile, wherein the pancreatic diluent is added to the pancreatic phase at a rate of 0.1 to 2.5 ml/min.

2. The assay of claim 1, wherein the porcine bile is collected from porcine gall bladders.

3. The assay of claim 1, wherein the pancreatin is present at a level of from about 10 mg/ml of pancreatic diluent to about 40 mg/ml of pancreatic diluent.

4. The assay of claim 1, wherein the porcine bile is present at a level of from about 0.25 to 0.75 ml per ml of pancreatic diluent.

5. The assay of claim 1, wherein the pancreatic diluent comprises $CHNaO_3$, $K_2HPO_4$, NaCl, $CaCl_2.2H_2O$, and urea.

6. The assay of claim 5, wherein the pancreatic diluent further comprises mucin.

7. The assay of claim 1, wherein the synthetic pancreatic juice is filtered prior to use.

8. The assay of claim 7, wherein the synthetic pancreatic juice is filtered using glass wool prior to use.

9. The assay of claim 1, wherein the gastric lipase is bacterial lipase.

10. The assay of claim 1, wherein the pepsin is porcine pepsin.

11. The assay of claim 1, wherein the gastric lipase is present at a level of from about from about 8.5 to about 250 µg/ml synthetic gastric juice.

12. The assay of claim 1, wherein the pepsin is present at a level of from about 85 to about 5000 µg/ml synthetic gastric juice.

13. The assay of claim 1, wherein the gastric diluent comprises NaCl, KCl, $KH_2PO_4$ and urea.

14. The assay of claim 1, wherein the salivary diluent comprises $NaHCO_3$, $K_2HPO_4.3H_2O$, NaCl, KCl, and $CaCl_2.2H_2O$.

15. The assay of claim 1, wherein the salivary enzyme is amylase.

16. The assay of claim 15, wherein the amylase is present at a level of from about 0.010 ml to about 2 mg/ml of slivary diluent.

17. The assay of claim 1, wherein the synthetic saliva is present as a 20% to 80% aqueous solution.

18. The assay of claim 1, wherein (i) the porcine bile is present at a level of from about 0.25 to 0.75 ml of pancreatic diluent, (ii) the gastric lipase is present at a level of from about 8.5 to about 250 µg/ml synthetic gastric juice, and/or (iii) the pepsin is present at a level of from about 85 to about 5000 µg/ml synthetic gastric juice.

* * * * *

UNITED STATES PATENT AND TRADEMARK OFFICE
CERTIFICATE OF CORRECTION

PATENT NO. : 10,191,062 B2
APPLICATION NO. : 15/039172
DATED : January 29, 2019
INVENTOR(S) : Jeff Pearson et al.

Page 1 of 1

It is certified that error appears in the above-identified patent and that said Letters Patent is hereby corrected as shown below:

In the Claims

At Column 18, Claim 16, Line 12 "at a level of from about 0.010 ml to about 2mg/ml of slivary" should be -- at a level of from about 0.01 µl/ml to about 2 mg/ml of salivary --.

Signed and Sealed this
Seventh Day of May, 2019

Andrei Iancu
*Director of the United States Patent and Trademark Office*